(12) United States Patent
Quincoces Suárez et al.

(10) Patent No.: US 9,381,169 B2
(45) Date of Patent: Jul. 5, 2016

(54) PHARMACEUTICAL COMPOSITION AND USE OF THE PHARMACEUTICAL COMPOSITION FOR THE TREATMENT, PROPHYLAXIS OR PREVENTION OF NEOPLASTIC DISEASES IN HUMANS AND ANIMALS

(75) Inventors: José Agustin Quincoces Suárez, São Paulo (BR); Durvanei Augusto Maria, São Paulo (BR); Paulo Celso Pardi, Praia Grande (BR); Fernanda Faião Flores, São Paulo (BR); Reginaldo Pereira Santos, São Paulo (BR); Daniela Gonçales Rando, São Paulo (BR)

(73) Assignees: UNIVERSIDADE BANDEIRANTE DE SÃO PAULO—ACADEMIA PAULISTA ANCHIETA S/C LT, São Paulo (BR); FUNDAÇÃO DE AMPARO À PESQUISA DO ESTADO DE SÃO PAULO—FAPESP, São Paulo (BR)

( * ) Notice: Subject to any disclaimer, the term of this patent is extended or adjusted under 35 U.S.C. 154(b) by 0 days.

(21) Appl. No.: 13/377,194

(22) PCT Filed: Nov. 11, 2009

(86) PCT No.: PCT/BR2009/000375
§ 371 (c)(1),
(2), (4) Date: Dec. 9, 2011

(87) PCT Pub. No.: WO2010/142007
PCT Pub. Date: Dec. 16, 2010

(65) Prior Publication Data
US 2012/0082703 A1    Apr. 5, 2012

(30) Foreign Application Priority Data
Jun. 9, 2009   (BR) ...................... 0902039

(51) Int. Cl.
*A61K 31/121*   (2006.01)
*A61K 31/337*   (2006.01)
*A61P 35/00*    (2006.01)
*A61P 35/04*    (2006.01)
*A61K 31/375*   (2006.01)
*A61K 31/675*   (2006.01)
*A61K 31/7048*  (2006.01)
*A61K 45/06*    (2006.01)

(52) U.S. Cl.
CPC ............. *A61K 31/121* (2013.01); *A61K 31/337* (2013.01); *A61K 31/375* (2013.01); *A61K 31/675* (2013.01); *A61K 31/7048* (2013.01); *A61K 45/06* (2013.01)

(58) Field of Classification Search
CPC ............. A61K 31/121; A61K 31/337; A61K 31/7048; A61K 31/675
USPC .................. 514/679, 733, 731, 449; 549/510; 568/325, 729
See application file for complete search history.

(56) References Cited

U.S. PATENT DOCUMENTS

2006/0258752 A1   11/2006   Vander Jagt et al.
2007/0010488 A1   1/2007    Youssef et al.
2007/0060644 A1*  3/2007    Vander Jagt et al. ......... 514/475

FOREIGN PATENT DOCUMENTS

| WO | 01/40188    | 6/2001 |
| WO | 2006/044379 | 4/2006 |
| WO | 2007/075772 | 7/2007 |
| WO | 2008/003155 | 1/2008 |

OTHER PUBLICATIONS

Adams et al., Biorganic & Medicinal Chemistry, 12:3871-3883 (2004). "Synthesis and biological evaluation of novel curcumin analogs as anti-cancer and anti-angiogenesis agents."
Flores et al., Applied Cancer Research, 28(2):72-79 (2008). "Antiproliferative and antimetastatic activity of DM-1, sodium 4-[5-(4-hydroxy-3-methoxyphenyl)-3-oxo-penta-1,4-dienyl]-2-methoxyphenolate, in B16F10 melanoma."

* cited by examiner

*Primary Examiner* — Sreeni Padmanabhan
*Assistant Examiner* — Irina Neagu
(74) *Attorney, Agent, or Firm* — David S. Resnick; Nixon Peabody LLP

(57) ABSTRACT

The present invention relates to pharmaceutical compositions comprising polyfunctional metal phenolates that have biological applications as an anticancer adjuvant, cytoprotective antimetastatic agents and antimutagenic agents when associated with chemotherapy drugs.
The present invention further relates to the use of said polyfunctional metal phenolates in the preparation of drugs for the treatment, prophylaxis or prevention of neoplasic diseases in humans and animals.

10 Claims, 27 Drawing Sheets

PHARMACEUTICAL COMPOSITION AND USE OF THE PHARMACEUTICAL COMPOSITION FOR THE TREATMENT, PROPHYLAXIS OR PREVENTION OF NEOPLASTIC DISEASES IN HUMANS AND ANIMALS

CROSS REFERENCE TO RELATED APPLICATIONS

This application is a 35 U.S.C. §371 National Phase Entry Application of International Application No. PCT/BR2009/000375 filed Nov. 11, 2009, which designates the U.S., and which claims benefit of Brazilian Application No. PI 0902039-0 filed Jun. 9, 2009, the contents of which are incorporated herein by reference in their entirety.

FIELD OF THE INVENTION

The present invention relates to polyfunctional metal phenolates and their biological applications as cytoprotective and/or enhancer adjuvants for commercial antitumorals, as protective adjuvants and as stimulators for bone marrow and as preventive agents for tumors. These compounds have antimutagenic and antimetastatic properties when associated with commercial chemotherapic agents, and reduce the toxicity thereof.

Specifically, this invention relates to pharmaceutical compositions comprising polyfunctional metal phenolates that have biological applications as anticancer adjuvants, cytoprotective agents, antimetastatic agents and antimutagenic agents when associated with chemotherapy compounds.

The present invention further relates to the use of polyfunctional metal phenolates in the preparation of drugs for the treatment, prophylaxis or prevention of neoplasic diseases in humans and animals.

BACKGROUND OF INVENTION

Cancer, or malign neoplasm, is a disease characterized by a population of cells that grows and divides indefinitely, invading and destroying various tissues in a process known as metastasis. Cancer is usually classified according to the tissue from which the cancerous cells originate, as well as the normal cell type they most resemble.

Nearly all cancers are caused by genetic abnormalities. These anomalies can be caused by carcinogenic agents (e.g. smoking, radiation, chemicals or infectious agents) or can be inherited, and thus are present in all cells from birth. Genetic abnormalities found in cancer typically affect two general classes of genes. The genes that promote cancer, oncogenes, are typically activated in cancer cells, providing those cells with new properties, such as hyperactive growth and division, protection against programmed cell death, loss of respect for normal tissue boundaries and the ability to become stable in several tissues. In addition, tumor suppressor genes are often inactivated in cancer cells, resulting in loss of normal functions of these cells as an accurate DNA replication, control over the cell cycle, orientation and adhesion within tissues, and interaction with protective cells of the immune system.

Once diagnosed, cancer is usually treated with a combination of surgery, chemotherapy and radiotherapy.

Most drugs used in cancer chemotherapy somehow interfere with the cell cycle and therefore are usually classified according to the effect thereof on the cell cycle: a) nonspecific chemo cycle—act on cells that are proliferating or not in the cycle, as for example, nitrogen mustard b) cycle-specific— act only on cells that are proliferating, such as cyclophosphamide and c) phase-specific—they act in certain phases of cell cycle, such as, methotrexate (S phase), placitaxel (M phase), etoposide (G2) and vincristine (M phase).

Chemotherapy can be done by applying one or more chemotherapeutic agents. The use of a single drug (monochemotherapy) is ineffective in inducing significant partial or complete responses in most tumors and currently has a very restricted use. Chemotherapy is of proven effectiveness and aims to achieve cell populations in different phases of the cell cycle, using the synergistic action of drugs, reduce the development of drug resistance and to promote greater response per dose.

The drugs used in cancer chemotherapy affect both the normal and the neoplasic cells. For this reason, the vast majority of treatments with conventional chemotherapy in either mono- or multidrug therapy is associated with a variety of undesirable side effects of these compounds, such as anemia, severe immunosuppression, alopecia, hepatotoxicity, mild gastrointestinal damage and peripheral neuropathy.

Most substances used in cancer treatment can damage DNA, causing the death of tumor cells. In addition to reaching the target cells, these substances can also be absorbed by normal cells and may cause the occurrence of mutations and genotoxic effects, leading to the appearance of secondary tumors. Thus, in assessing the clastogenic potential of chemicals used in chemotherapy, one seeks to implement treatment protocols and/or other drugs that can minimize the effects of the used agents.

Anticancer drugs such as cyclophosphamide, etoposide and paclitaxel, are used in antitumor therapy, but have great potential to cause mutagenicity in bone marrow cells, and DNA damage in patients taking said medicine alone or in combination (Mazu et al. Mutat. Res, 309 (2): pp. 219-213, 1994, Shuko, Y. Human and exp. Toxicol., 23 (5):245-250, 2004, Branham, M T Mutat. Res., 560 (1): 11-17, 2004, Huang, R. CA Cancer J. Clin., 59:42-55, 2009). Thus, the decline of the mutagenic action of antitumor compounds such as paclitaxel, cyclophosphamide and etoposide is related to the association of some drugs such as dexrazoxane, amifostine and mesna.

However, these co-adjuvant drugs have important disadvantages. Dexrazoxane reduces the toxicity of etoposide, but has significant side effects as well as rates of cell damage in an excess of 45% [Attia et al. Cancer Chem. Pharmacol., 2009 (Epub ahead of print)]. Amifostine has reduced toxicity when used in combination with cisplatin or paclitaxel (Marcu L G. Eur J Cancer Care (Engl), 18 (2): 116-123, 2009), but it has from 50 to 60% of cell damages. Mesna in combination with paclitaxel has moderate antimutagenic action and the presence of undesirable side effects (Souza et al., Rev. Bras. Hemat. Hemoter., 22 (2): 123-128, 2000, Chen et al. Gen. Cancer There., 14 (12): 935-944, 2007; Vilar et al. Braz. J. Biol., 68 (1): 141-147, 2008).

In light of the above, it is desirable to develop adjuvant components to reduce the side effects of cancer chemotherapeutic agents and to increase their toxicity to tumor cells.

Metal salts of the compound 1,5-bis(4-hydroxy-3-methoxyphenyl)penta-1,4-dien-3-one, such as sodium 4-[5-(4-hydroxy-3-methoxy-phenyl)-3-oxo-penta-1,4-dienil]-2-methoxyphenolate (metal phenolate) were obtained by J. Quincoces and colleagues (patent documents PCT/BR2007/000175 and PI0602640-0), and showed significant antiproliferative activity in tumor cell lines. In addition, these compounds were also able to inhibit the formation of metastases (Faião-Flores et al., Applied Cancer Res, 28 (2): 72-79, 2008). However, until now there have not been described in the literature that these compounds do potentiate the adjuvant, antimetastatic, cytoprotective and antimutagenic actions when associated with other antitumor drugs.

OBJECT OF THE INVENTION

The present invention aims at the use of polyfunctional metal phenolates as adjuvants in combination with antitumor drugs in order to enhance their antitumor effects in addition to preventing adverse effects on bone marrow and on the immunohematological system.

It is another objective of the present invention the use of polyfunctional metal phenolates in combination with antitumor drugs for the prevention of the appearance of tumors and inhibition of migration of tumor cells to other tissues and organs (metastasis).

It is another objective of the present invention the use of polyfunctional metal phenolates in combination with antitumor drugs such as antimutagenic agents of conventional anticancer drugs that cause mutagenesis.

A more specific objective of the present invention is to provide pharmaceutical compositions comprising polyfunctional metal phenolates in association with one or more anticancer drugs, and one or more among a vehicle, excipient, physiologically acceptable diluent or solvent.

It is still another object of the present invention the use of polyfunctional metal phenolates for the preparation of drugs for the treatment, prophylaxis or prevention of neoplasic diseases in humans and animals.

DEFINITIONS

So as to render the present patent application readable the abbreviation DM-1 is used several times. This abbreviation refers to the compound sodium 4-[5-(4-hydroxy-3-methoxy-phenyl)-3-oxo-penta-1,4-dienil]-2-methoxy-phenolate.

DESCRIPTION OF FIGURES

The following figures are part of this specification and are included to illustrate specific aspects of the invention. The object of the present invention can be better understood with reference to one or more of these figures, in combination with detailed description of the preferred embodiment presented herein.

DETAILED DESCRIPTION OF THE INVENTION

Figure 1:
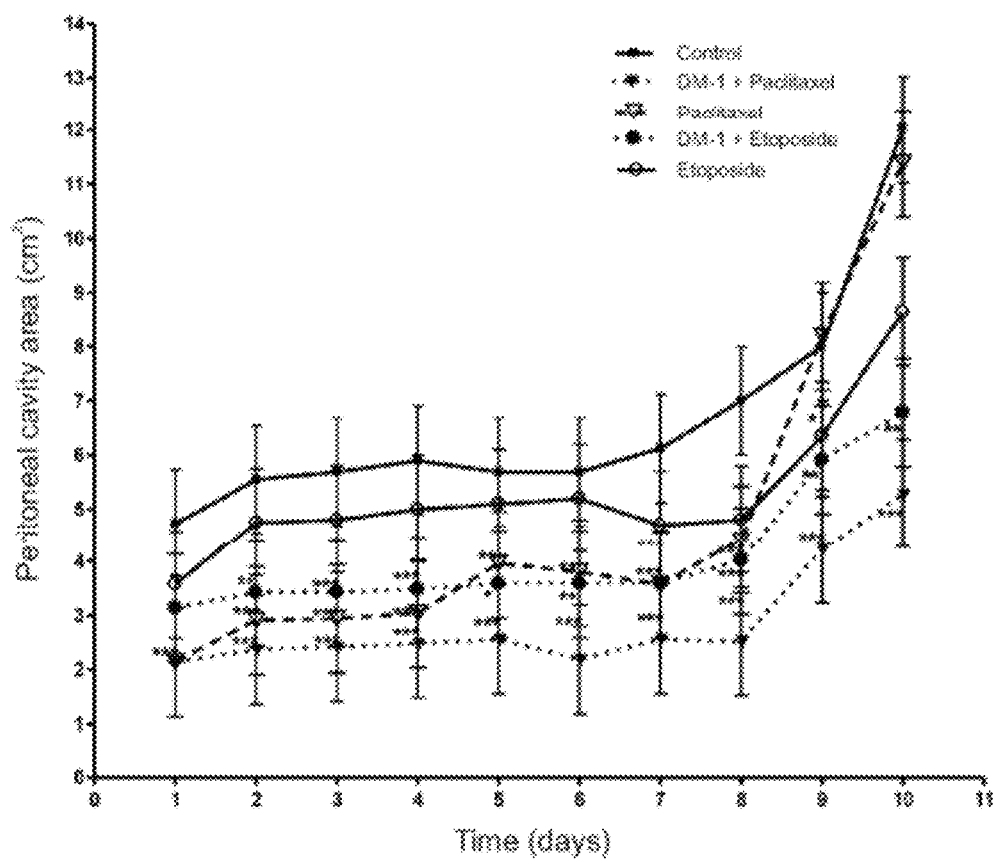
FIG. 1 shows the variation in the tumor area of mammary adenocarcinomas in mice treated with paclitaxel, etoposide, placitaxel in association with DM1 and etoposide in association with DM1 compared to control (untreated).

The present invention relates to metal phenolate of general formula I:

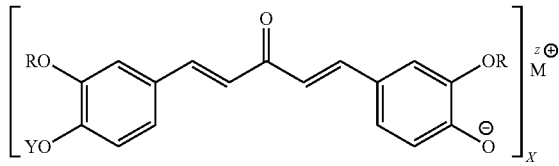

wherein

R is, in each occurrence separately, a hydrogen atom, an alkyl group, a prenyl group, an acetyl group, a benzoyl group, or a metal cation;

Y is, at each occurrence separately, a hydrogen atom, an alkyl group, a prenyl group, an acetyl group, a benzoyl group, or a metal cation;

X can be, in each case separately, 1, 2 or 3;

$M^{z+}$ is, in each separate occurrence, a monovalent cation, a divalent cation, or a trivalent cation.

The phenolate polyfunctional metal compounds described in the present invention exhibit an unexpected technical effect on potentiating the antitumor activity of anticancer drugs, acting as a cytoprotective adjuvant protecting and stimulating the bone marrow and as preventive agents for tumors. These compounds also have antimetastatic and antimutagenic properties when associated with antitumor drugs, reducing the toxicity thereof. The compounds herein described also have the ability to induce cell death (apoptosis, anoiquis) in proliferative diseases of humans and animals and, hence, inhibit growth and prevent the migration of human and animal tumors.

Thus, the present invention relates to the use of these compounds in combination with antitumor drugs for the treatment, prophylaxis or prevention of neoplasic diseases and for the prevention of metastatic lesions in proliferative and/or degenerative diseases. In particular, this invention relates to the use of these compounds in the treatment, prophylaxis or prevention of neoplasic diseases caused by lung cancer, breast cancer and breast cancer resistant to multiple drugs, non-melanoma skin cancers and melanomas, lymphoid leukemia, acute myeloid and chronic erythroleukemia, myelodysplasia and cancers of the colon, ovary, uterus, kidney, pancreas, prostate, soft tissue sarcomas, hepatocellular carcinomas, osteosarcomas, central nervous system, neuroblastomas, astrocytomas, oropharynx, thyroid, gastric, prostate and cancers of the male reproductive system.

The present invention further relates to pharmaceutical compositions comprising the polyfunctional metal phenolates of the present invention and present biological applications thereof as an anticancer adjuvant, cytoprotective antimetastatic agents and antimutagenic agents when associated with chemotherapy.

More specifically, the present invention relates to pharmaceutical formulations comprising one or more metal phenolates as described in the present invention, at least one antitumor drug and one or more of among a vehicle, excipient, physiologically acceptable diluent or solvent.

For the pharmaceutical compositions comprising one or more metal phenolates described in the present invention, the active ingredient can be prepared according to conventional techniques of pharmaceutical combinations [see Remington's Pharmaceutical Sciences, 18th Ed, Mack Publishing Co., Easton, Pa., USA (1990)]. Typically, an amount of active ingredient is mixed with a pharmaceutically acceptable excipient. The excipient may have a variety of formulas, depending on the form of preparation desired for administration, e.g. intravenous, oral or parenteral. The compositions may also contain stabilizing agents, preservatives and the like.

For oral administration, the compounds can be formulated in solid or liquid preparations such as capsules, pills, tablets, lozenges, molasses, powders, suspensions or emulsions. In the preparation of compositions in oral dosage form, some of the usual pharmaceutical media may be employed, for example: water, glycols, oils, alcohols, artificial flavors, preservatives, dyes, suspensions and the like in the case of oral liquid preparations (e.g. suspensions, elixirs and solutions), or vehicles such as starches, sugars, diluents, granulating agents, lubricants, binders, disintegrating agents and the like in the case of oral solid preparations (such as, for example, powders, capsules and tablets). Due to the ease of administration thereof, tablets and capsules represent the most advantageous form of oral dosing, wherein the solid pharmaceutical excipients are obviously employed. If desired, tablets can be sugar coated or enteric coated by standard techniques for protectors. The immunotherapeutic described in the present invention may be encapsulated to render it stable to passage through the gastrointestinal tract while allowing the passage through the blood-brain barrier, as described in the patent document WO 96/11698.

For parenteral administration, the compound can be dissolved in a pharmaceutically acceptable media and be administered as a solution or a suspension. Examples of suitable vehicles are: water, saline, dextrose solutions, fructose solutions, ethanol, or oils of animal, vegetable or synthetic sources. Other vehicles may also contain other ingredients, for example: preservatives, binding agents, solubilizing agents, buffers and the like. When the compounds are administered intrathecally, they may also be dissolved in cerebrospinal fluid.

The pharmaceutical compositions should contain from about 0.0001 to 99%, preferably from about 0.001 to 50%, more preferably from about 0.01 to 10% by weight of one or more of the metal phenolates described in the present invention regarding the total weight of the composition. In addition to one or more of the metal phenolates described in the present invention, pharmaceutical compositions and medicines may also contain other pharmaceutically active compounds. When used in conjunction with other pharmaceutically active compounds, the metal phenolates of the present invention may be provided in the form of a cocktail of drugs. A drug cocktail is a mixture of some compounds used in this invention with another drug or agent. In this embodiment, a common vehicle of administration (e.g., pill, tablet, implant, pump, injectable solution, etc.) may contain both the said composition in combination with additional active agents. The individual drugs in the cocktail are, each, administered in a therapeutically effective amount to achieve the desired effects.

A variety of routes of administration for the metal phenolates and pharmaceutical compositions described in the present invention is available. The particular mode to be selected will depend on the particular compound selected, the severity of the disease state being treated and the dose required for therapeutic efficacy. The methods of the present invention generally can be practiced using any mode of administration biologically acceptable, i.e. in any mode to produce effective levels of active compounds without causing clinically adverse reactions. Such modes of administration include: oral, rectal, sublingual, topical, nasal, transdermal or parenteral. The term "parenteral" includes: subcutaneous, intravenous, epidural, irrigation, intramuscular, release pumps, or infusion.

Thus, administration of one or more metal phenolates described in the present invention can be achieved using all appropriate delivery means, including: (a) pump, (b) microencapsulation (see patent documents U.S. Pat. No. 4,352,883, U.S. Pat. No. 4,353,888 and U.S. Pat. No. 5,084,350), (c) polymer implants for continuous release (see patent document U.S. Pat. No. 4,883,666), (d) macroencapsulation (see patent documents U.S. Pat. No. 5,284,761, U.S. Pat. No. 5,158,881, U.S. Pat. No. 4,976,859 and U.S. Pat. No. 4,968,733 and patent applications WO92/19195 and WO95/05452), (e) non-encapsulated cell grafts in the central nervous system (see patent documents U.S. Pat. No. 5,082,670 and U.S. Pat. No. 5,618,531), (f) subcutaneous injection, intravenous, intraarterial, intramuscular, or other appropriate place, or (g) oral administration in capsule, liquid, tablet, pill or extended release formulation.

Preferably the pharmaceutical compositions of this invention are to be intravesical infusions. One or more metal phenolates described in this invention are preferably administered in a therapeutically effective amount. The term "therapeutically effective amount" or simply "effective amount" of an active compound, as used herein, should be understood as an average enough amount of phenolate metal to treat the disease, so as to maintain a reasonable risk/benefit ratio applicable to any medical treatment. The actual amount administered, the rate and time management course, depend on the nature and severity of the condition being treated. Prescription of treatment, e.g. decisions on dosage, duration, etc. depend on the monitoring of the disease being treated, on the patient's individual condition, the route and method of administration, and other factors typical of knowledge of clinicians who are within the responsibilities of general practitioners and specialists.

The dosage may be adjusted appropriately to achieve desired levels of the metal phenolate, locally or systemically.

The present invention further relates to the use of the polyfunctional metal phenolates described in this invention in the preparation of medicines for the treatment, prophylaxis or prevention of neoplasic diseases in humans and animals.

Thus, another aspect of this invention relies on the use of the compounds of the present invention to manufacture medicines for the treatment, prophylaxis or prevention of neoplasic diseases, and metastatic lesions in proliferative and/or degenerative diseases. In particular, the compounds described herein can be used to treat or prevent or to manufacture medicines for the treatment, prophylaxis or prevention of neoplasic diseases caused by lung cancer, breast cancer and breast cancer resistant to multiple drugs, non-melanoma skin cancers and melanomas, lymphoid leukemia, acute myeloid and chronic erythroleukemia, myelodysplasia, and cancers of the colon, ovary, uterus, kidney, pancreas, prostate, soft tissue sarcomas, hepatocellular carcinomas, osteosarcomas, central nervous system, neuroblastomas, astrocytomas, oropharynx, thyroid, gastric, prostate and cancers related to the male reproductive system.

EXAMPLES

To allow a better understanding of the present invention and clearly demonstrate the technical advances obtained are now presented as examples the results of different experiments carried out with respect to this invention.

Example 1

Enhancement of Antitumor Activity of Paclitaxel and Etoposide Chemotherapy by Means of the Concurrent Use of the Compound DM-1 in Experimental Mammary Adenocarcinoma (an Ehrlich Tumor)

a) Maintenance of the Tumor In Vivo and Retrieval of Tumor Cells in Ehrlich Ascites.

As an experimental model of mammary adenocarcinoma, we used the Ehrlich tumor in mice of the Balb-c strain, with approximately 2 months of age and weighing between 20 to 25 grams. The maintenance of the tumor in vivo was performed by intraperitoneal administration of $10^7$ cells every seven days.

b) Animals and Experimental Design

We used 50 mice of the Balb-c strain, females and males, with approximately 25 g, aged approximately 6 to 8 weeks, with diet and water ad libitum, that were divided into 5 groups:

CONTROL GROUP—10 animals implanted with tumor, which after 7 days of application, received daily intraperitoneal doses of saline 0.9%;

Paclitaxel-treated group—10 animals implanted with tumor, which after 7 days of application, received intraperitoneal doses of paclitaxel chemotherapy in the 1st, 5th and 10th days of treatment;

Group treated with paclitaxel and DM-10—10 animals with implanted tumors, which after 7 days of application, were dosed daily intraperitoneal compound DM-1, associated with doses of the chemotherapeutic agent paclitaxel in the 1st, 5th and 10th days of treatment;

Etoposide-treated group—10 animals implanted with tumor, which after 7 days of application, received intraperitoneal doses of etoposide chemotherapy in the 1st, 5th and 10th days of treatment;

Group treated with etoposide and DM-10—10 animals with implanted tumors, which after 7 days of application, were dosed daily intraperitoneal compound DM-1, associated with doses of the chemotherapeutic agent etoposide on the 1st, 5th and 10th days of treatment.

c) Administration of the Compounds Paclitaxel, Etoposide and DM-1,

The compound DM-1 was administered daily at a concentration of 1.6 nM/kg, calculated from the IC 50% inhibitory activity in vitro. Paclitaxel and etoposide were administered at concentrations of 15 μM/Kg and 3.73 mM/kg, respectively, by intraperitoneal slow infusion in treatment regimens described in the literature on days 1, 5 and 10, after the 7th day of tumor implantation. The compounds were administered separately.

d) Evaluation of Tumor Growth

Tumor growth in mice was measured by the dimensions on the longitudinal and transverse abdominal cavity, with the aid of a digital caliper. These measurements were used to calculate the area, mass, and tumor burden. The mean area (A), mass (M) and tumor burden (C) were calculated using the following equations, respectively:

$$A = n\pi 2; L2 \times T = M/2$$

(where L is the measured longitudinal and transverse extent of the T waist circumference).

The groups of animals treated with paclitaxel and etoposide in combination with compound DM-1 showed a significant reduction in tumor growth compared to the control group and groups treated only with etoposide and paclitaxel chemotherapy, with median values of tumor area of $5.3 \pm 1.0$ cm$^2$ in the group treated with paclitaxel-1 DM, $6.8 \pm 1.1$ cm$^2$ the group treated with etoposide and DM-1, while the control group showed mean values of $12.0 \pm 1.1$ cm$^2$, $11.4 \pm 1$ cm$^2$ in the group treated with paclitaxel and $8.6 \pm 1.0$ cm$^2$ in group treated with etoposide. The efficacy of treatment increased by 115% and 27% in the groups treated with chemotherapeutic agents paclitaxel and etoposide, respectively (FIG. 1).

e) Evaluation of Survival Rate

Figure 2:
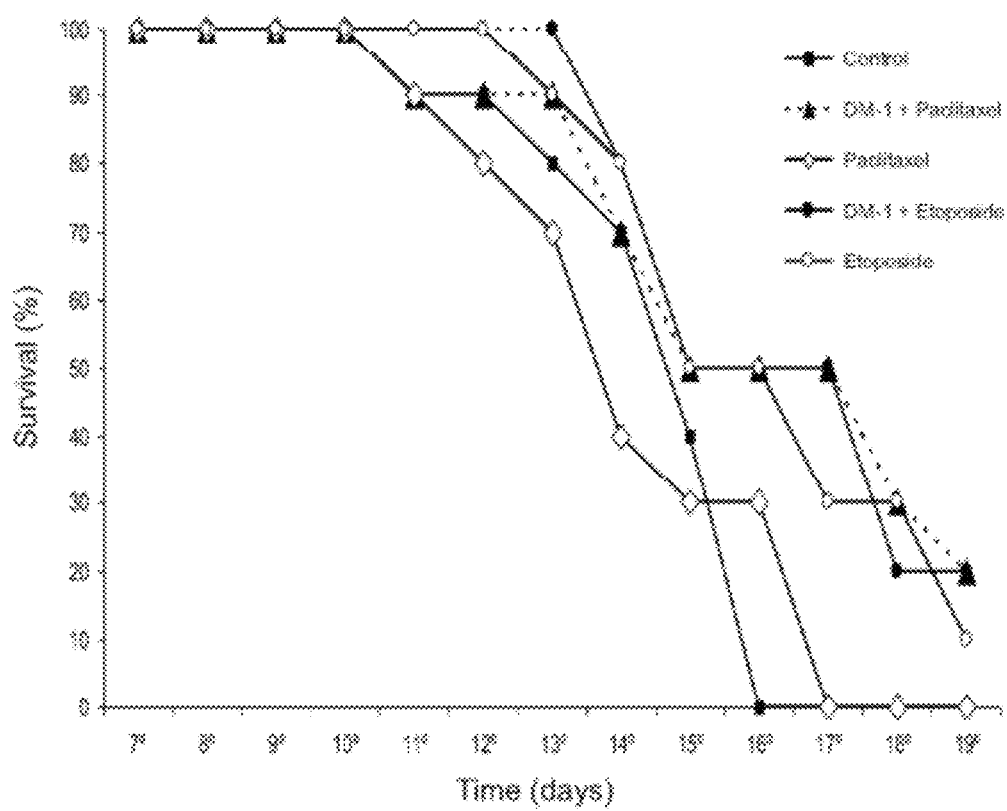
FIG. 2 shows the survival rate of groups of mice with breast adenocarcinoma treated with paclitaxel, etoposide, placitaxel in association with DM1 and etoposide in association with DM1 compared to control (untreated).

The survival rate was calculated by Kaplan-Meier method. Animals treated with chemotherapeutic agents paclitaxel and etoposide showed increased survival of 20% and 10% respectively, when associated with the compound DM-1 (FIG. 2).

f) Evaluation of the Number of Metastases.

Figure 3:
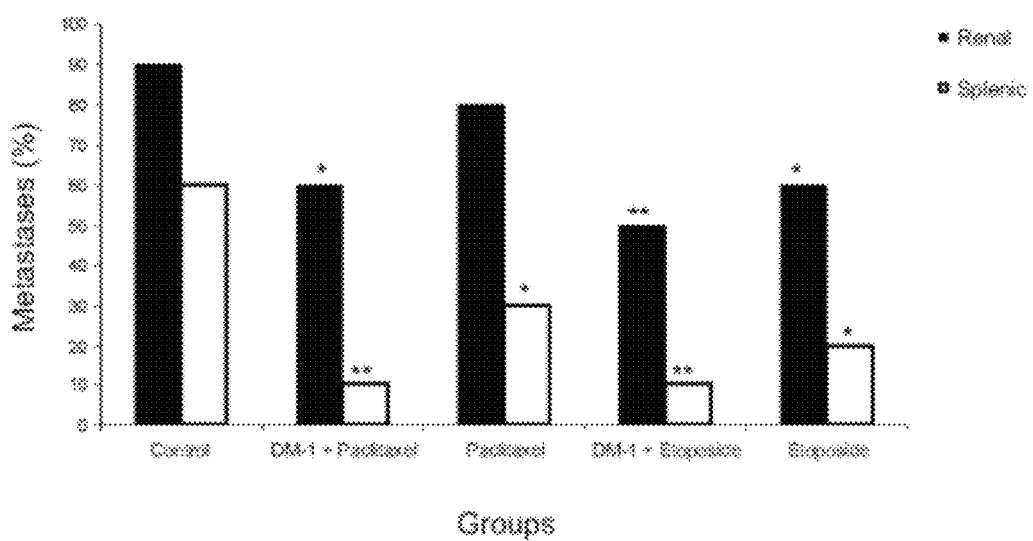
FIG. 3 shows the number of renal and splenic metastasis in the groups of mice with breast adenocarcinoma treated with paclitaxel, etoposide, placitaxel in association with DM1 and etoposide in association with DM1 compared to control (untreated).

The results showed that animals treated with paclitaxel and etoposide chemotherapy when combined with DM-1 compound, the percentage of internal metastases decreased significantly. The group treated with paclitaxel and DM-1 had a decrease of metastases in 30% kidney and 50% in the spleen while the treated group Etoposide+DM-1 showed 30% decrease in kidney and 40% in the spleen. The groups treated only with etoposide or paclitaxel chemotherapy showed a reduction in the number of metastases of 10% and 30% and 30% and 50%, kidney and spleen, respectively (FIG. 3).

g) Evaluation of the Macroscopic Volume of the Spleen and Splenic

Figure 4:
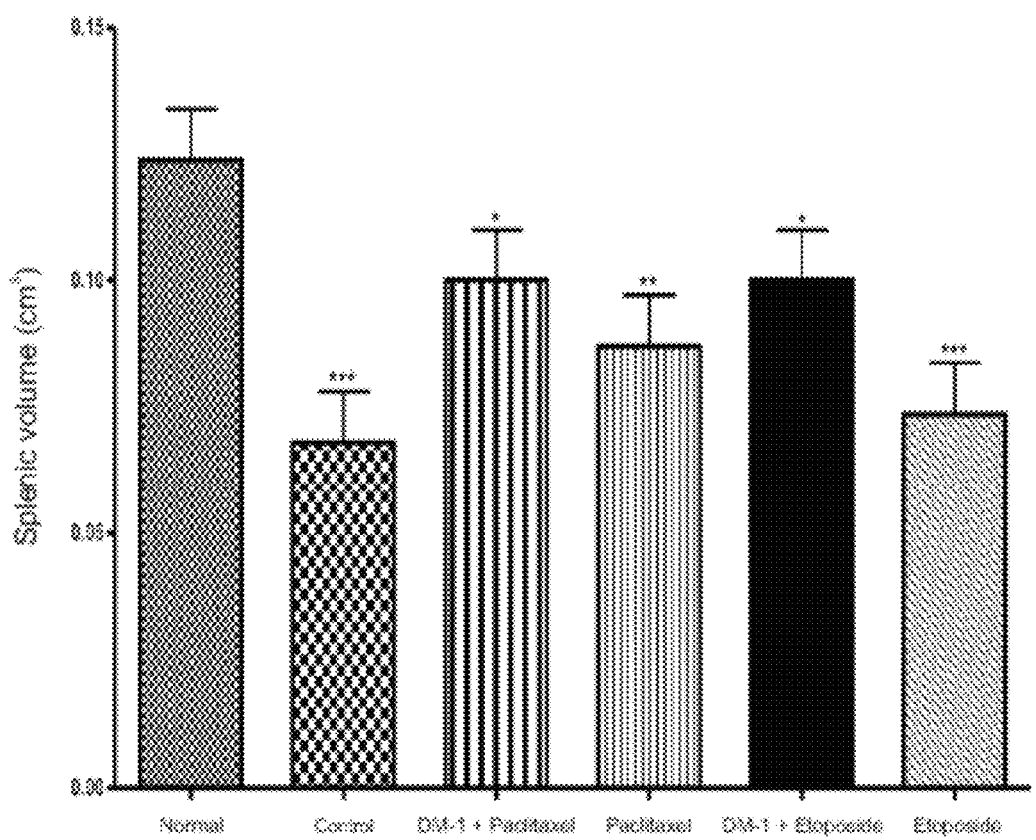
FIG. 4 shows the change in spleen volume in mice bearing mammary adenocarcinoma treated paclitaxel, etoposide, placitaxel in association with DM1 and etoposide in association with DM1 compared to control (untreated).

The spleens of animals from all experimental groups were analyzed for the display of nodes and metastases. The results showed that the spleen volume in the groups treated with the chemotherapeutic agents paclitaxel and etoposide in combination with the compound DM-1 did not differ in spleen volume of normal animals. Also, note that the administration of paclitaxel and etoposide chemotherapy without the compound DM-1 makes the spleen volume similar to that of untreated animals (FIG. 4).

Thus, the immunosuppression that occurs in animals with Ehrlich ascites tumor found in the control group was suppressed by the administration of the compound DM-1 in all experimental protocols. These results show, therefore, that the compound DM-1 acts as an immunomodulator or chemoprotetor.

Example 2

Enhancement of Antitumor Activity of Paclitaxel and Etoposide Chemotherapy by Means of the Concurrent Use of the Compound DM-1 in B16F10 Melanoma a) Implementation of B16F10 Melanoma Tumor Cells Groups of mice of the C57Bl/6J strain were injected subcutaneously dorsally with 5×104 B16F10 melanoma tumor cells under sterile conditions. The animals were observed every 72 hours and tumor growth monitored until the average diameter of 0.5 cm$^2$.

b) Animals and Experimental Design

We used 50 mice of strain C57BL/6J, males and females, with approximately 25 g, aged approximately 6 to 8 weeks, with diet and water ad libitum, that were divided into 5 groups:

Control group—10 animals with B16F10 melanoma tumor, which after the 11th day of tumor implantation, received daily intraperitoneal doses of saline 0.9%;

Paclitaxel-treated group—10 animals with B16F10 melanoma tumor, which after the 11th day of tumor implantation, received intraperitoneal doses of paclitaxel chemotherapy in 1, 5 and 9 days of treatment;

Group treated with paclitaxel and DM-10—10 animals tumor-bearing melanoma B16F10, which after 11 of the implant tumor, were dosed daily intraperitoneal compound DM-1, associated with doses of the chemotherapeutic agent paclitaxel in 1, 5 and 9 days of treatment;

Group pre-treated with the DM-1 compound prior to the implant of B16F10 melanoma cells—10 animals were treated with daily doses of the compound DM-1 for 14 days before implantation of tumor cells. After 14 days, the animals received implantation of B16F10 melanoma cells and received no treatment until the end of the experiment.

Group pre-treated with the DM-1 compound prior to the implant of B16F10 melanoma cells and post-treated with DM-1 compound—10 animals were treated with daily doses of the compound DM-1 for 14 days before implantation of tumor cells. After 14 days, the animals received implantation of B16F10 melanoma cells and continued to receive daily treatment with the compound DM-1 for another 14 days.

c) Administration of the Compounds DM-1 Paclitaxel

The compound DM-1 was administered daily at a concentration of 0.83 nM/kg, calculated from the IC 50% inhibitory activity in vitro. Paclitaxel was administered at a concentration of 15 μM/Kg, via intraperitoneal slow infusion, the treatment regimens described in the literature on days 1, 5 and 10, after the 7th day of tumor implantation. The compounds were administered separately.

d) Assessment of Tumor Growth.

The groups of animals treated with paclitaxel chemotherapy associated with compound DM-1 showed a significant reduction in the growth of dorsal melanoma, while the control group presented an exponential increase in their growth.

Figure 5:
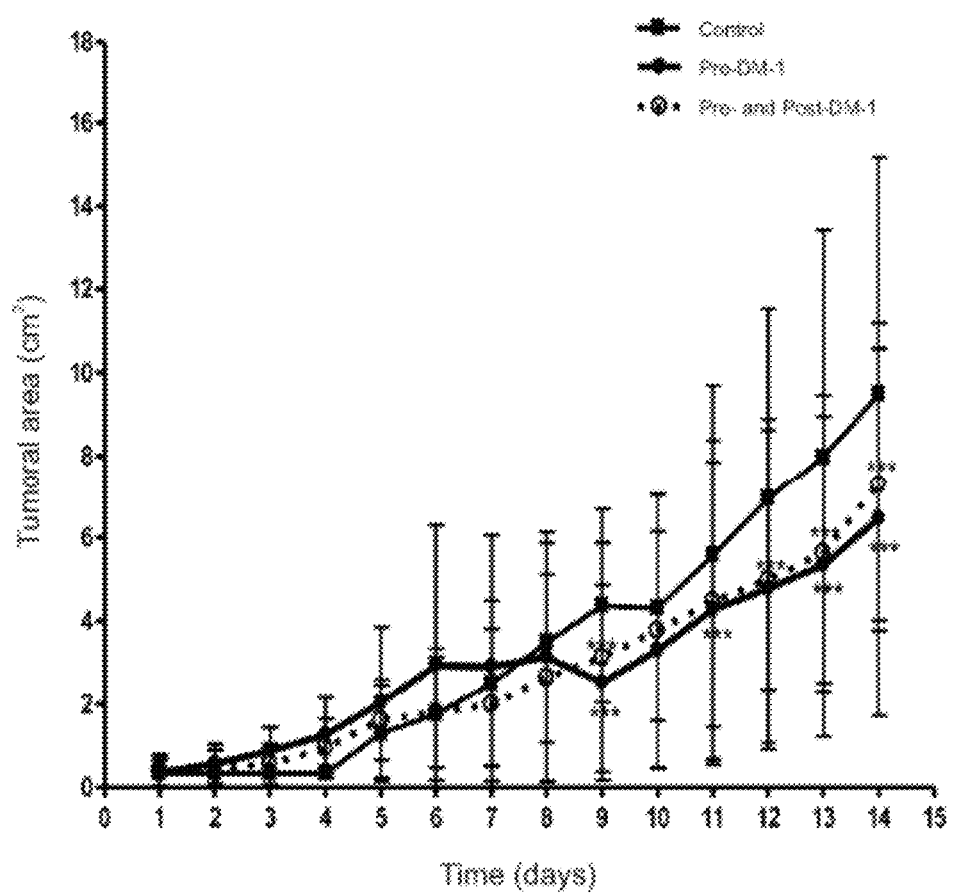
FIG. 5 shows the variation of the B16F10 melanoma tumor area in mice treated with the compound DM-1 (pre and post treated and treated with DM-1) compared to control (untreated).

The groups treated with DM-1 showed a decrease in dorsal tumor area, with average values of $6.5 \pm 1.7$ cm$^2$ in the group pretreated with DM-1, $7.3 \pm 1.3$ cm$^2$ in group pre and post treated with DM-1 (FIG. 5).

Figure 6:
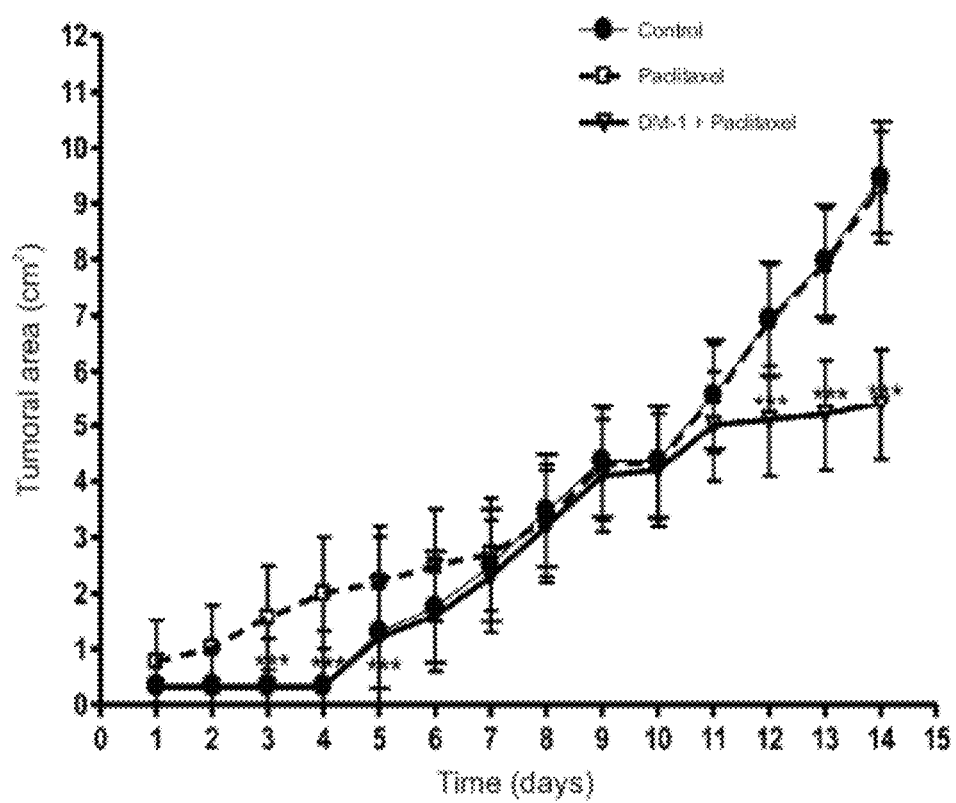
FIG. 6 shows the variation of the B16F10 melanoma tumor area in mice treated with paclitaxel and placitaxel in association with DM1 compared to control (untreated).

The group treated with paclitaxel and DM-1 achieved a reduction of tumor area in relation to the group treated with paclitaxel, of 5.1±9.4 and ±1.5 cm² 1.1 cm², respectively. The control group showed values of 9.5±2.9 cm² proving effective antitumor activity of groups treated with the combination of the compound DM-1 (FIG. 6).

e) Evaluation of Survival Rate

Figure 7:
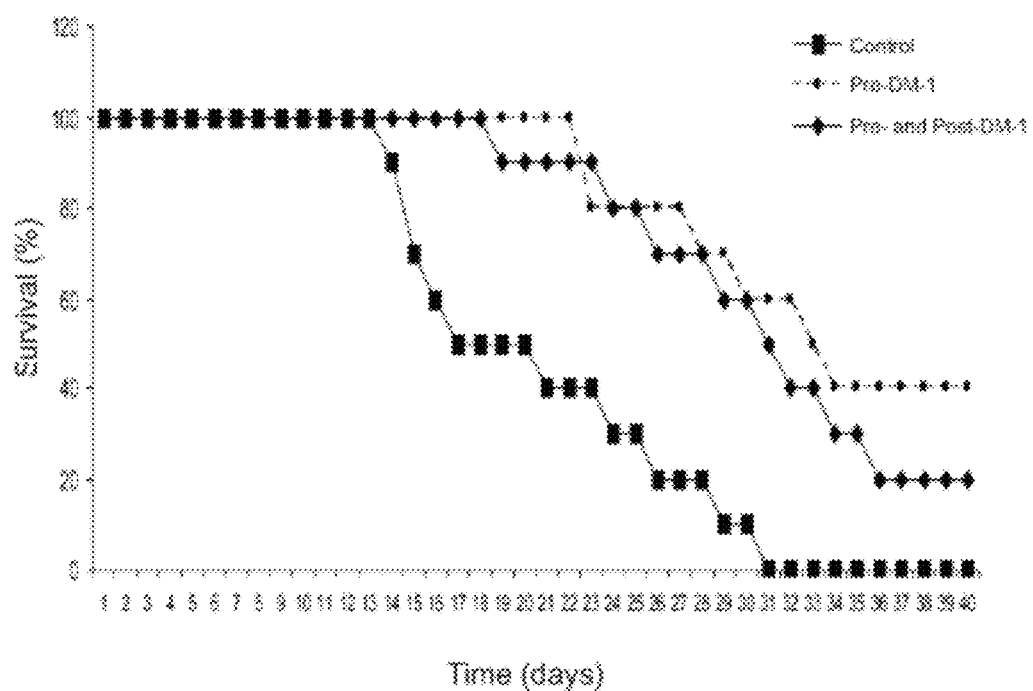
FIG. 7 shows the survival rate of groups of mice bearing B16F10 melanoma treated with the compound DM-1 (pre and post treated and treated with DM-1) compared to control (untreated).
Figure 8:
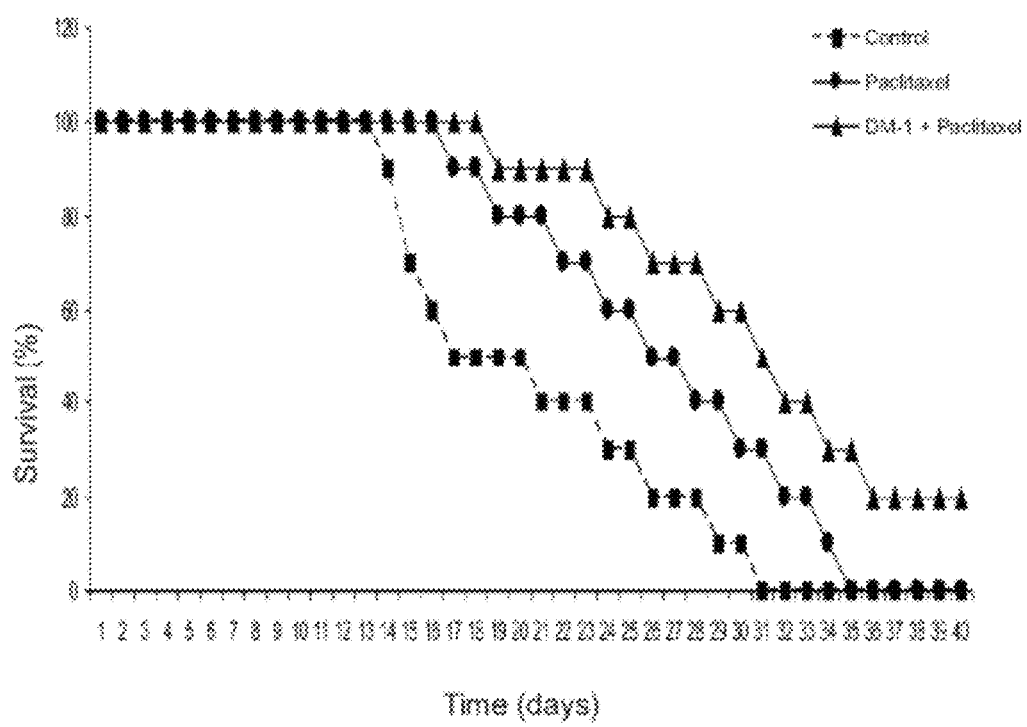
FIG. 8 shows the survival rate of groups of mice bearing B16F10 melanoma treated with paclitaxel and placitaxel in association with DM1 compared to control (untreated).

The compound DM-1 in all treatment regimens, increased significantly the survival rate of animals with dorsal melanoma. Administration of the compound in the group pre-treated with DM-1 increased 50% survival rate of animals. In the group pre- and post-DM-1 increased the survival rate was 30%, and the group treated with paclitaxel-1 DM and 30%. The group treated with paclitaxel showed no significant changes in survival of these animals (FIGS. 7 and 8).

f) Evaluation of the Number of Metastases

Figure 9:
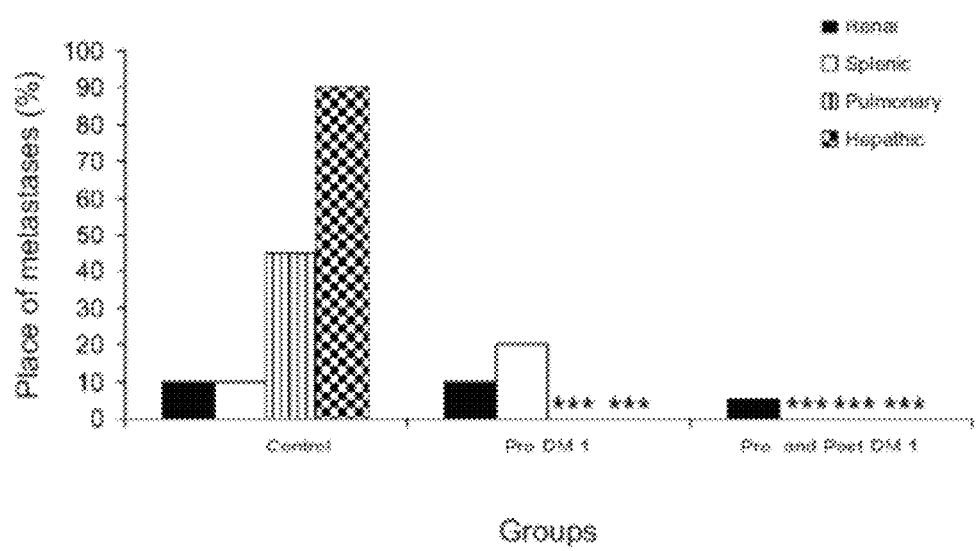
FIG. 9 shows the distribution and location of metastases in internal organs in mice bearing B16F10 melanoma with the compound DM-1 (pre and post treated and treated with DM-1) compared to control (untreated).
Figure 10:
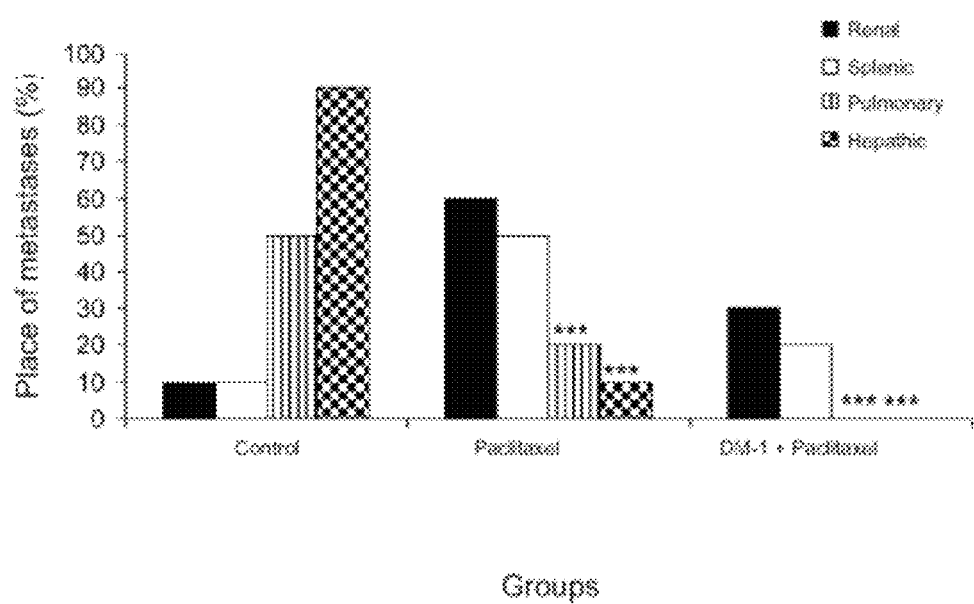
FIG. 10 shows the distribution and location of metastases in internal organs in mice bearing B16F10 melanoma treated with paclitaxel and placitaxel in association with DM1 compared to control (untreated).

The results showed that in all regimens wherein the DM-1 compound was administered the percentage of internal metastases decreased significantly. In the group pre-treated with DM-1 was observed an inhibition of the formation of lung metastases and liver, as well as pre and post groups treated with DM-1 and treated with paclitaxel in combination with DM-1. The association of DM-1 treatment to paclitaxel chemotherapy showed that the compound is extremely effective, the association of DM-1 potentiated the inhibitory effect of metastasis formation of paclitaxel (FIGS. 9 and 10).

g) Hematologic Evaluation

The blood of animals with B16F10 melanoma tumor was harvested in the 6th and 14th day during treatment with the compound DM-1 and prior to the inoculation of B16F10 cells. In the charts, collections for the day 6 were named 1A, while those relating to day 14 were named 2A. After implantation, tumor blood were collected in the second, sixth and tenth days of treatment (after treatment with DM-1) in all groups of animals, and these collections were named 1B and 2B and 3B, respectively.

Figure 11:
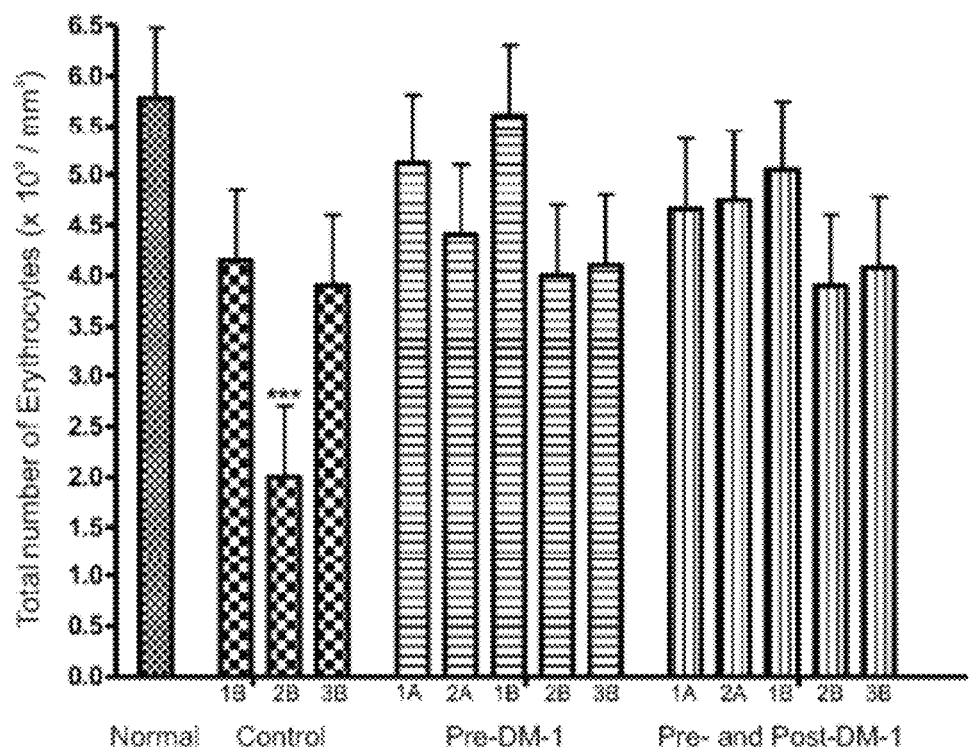
FIG. 11 shows the evaluation of the total number of red blood cells of normal mice and tumor melanoma B16F10 groups of animals pre-treated with the compound DM-1 and pre and post treated with DM-1 on days 6 and 14 prior to implant (1a and 2A) and the second, on days 6 and 10 after initiation of treatment (1B, 2B and 3B) compared to the control group.
Figure 12:
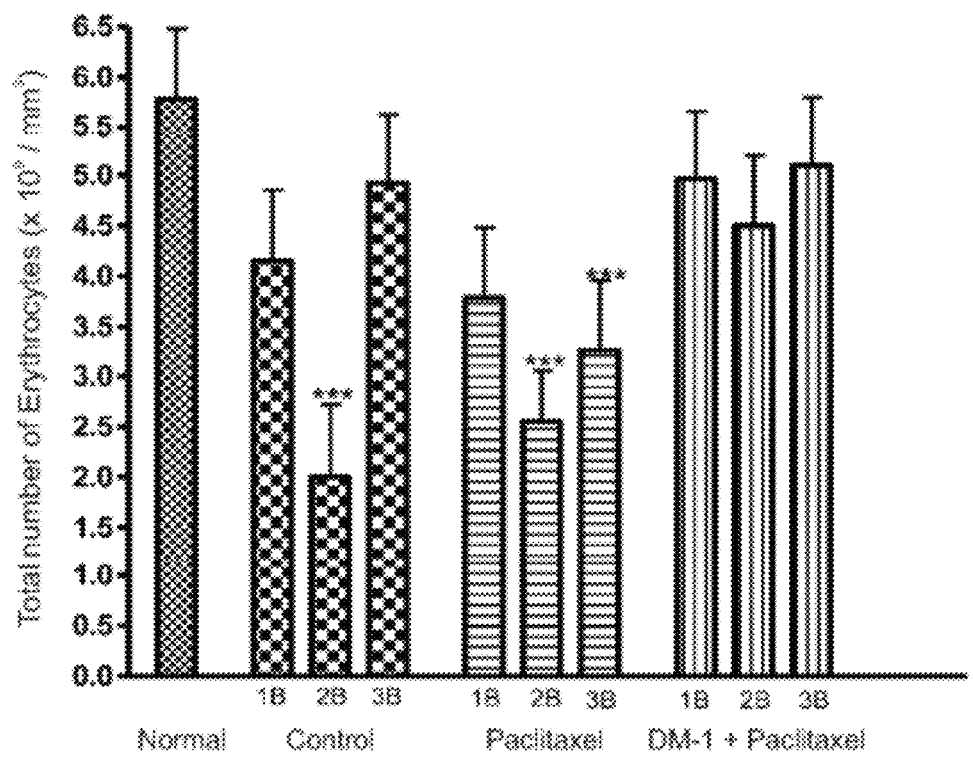
FIG. 12 shows the evaluation of the total number of erythrocytes and normal animals with B16F10 melanoma tumor in groups of animals pre-treated with paclitaxel and placitaxel in association with DM1 on days 2, 6 and 10 after initiation of treatment (1B, 2B and 3B) compared to the control group.

The analysis of erythrocytes of animals treated with DM-1 showed that treatment with DM-1 does not induce anemia. Furthermore, the compound DM-1 was effective in preventing the side effects of bone marrow suppression. The compound DM-1 also modulates the effects of anemia caused by tumors in the groups treated with DM-1 and DM-1 in combination with paclitaxel (FIGS. 11 and 12).

Figure 13:
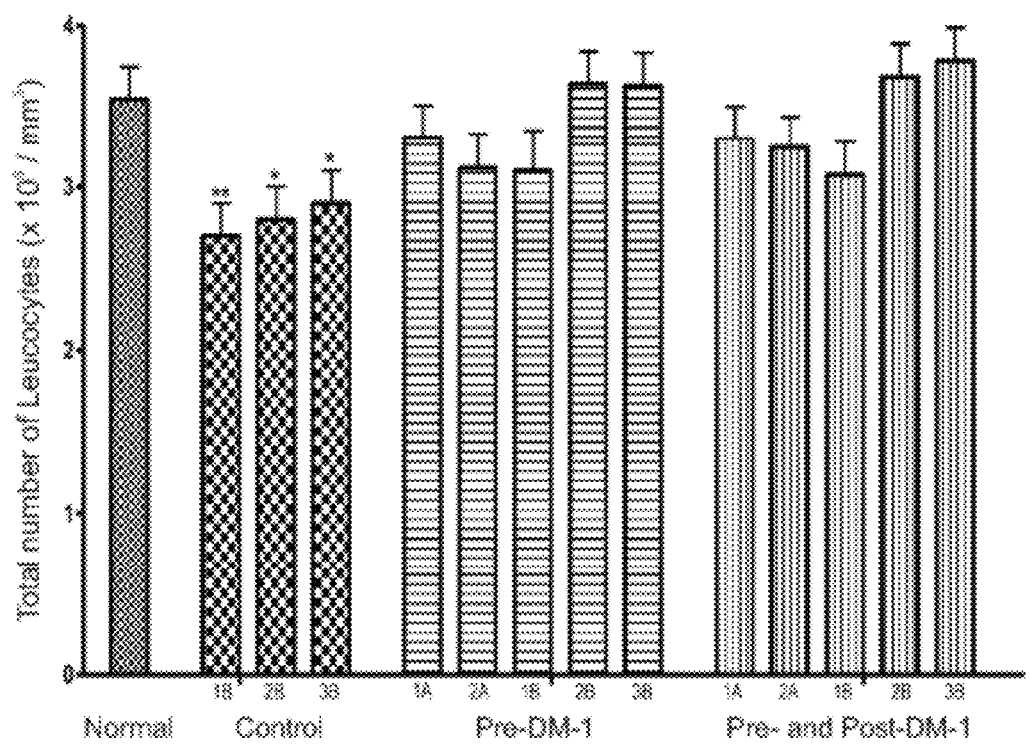
FIG. 13 shows the evaluation of the total white blood cells of normal mice and tumor melanoma B16F10 in groups of animals pre-treated with the compound DM-1 and pre and post treated with DM-1 on days 6 and 14 prior to implant (1a and 2A) and on days 2, 6 and 10 after initiation of treatment (1B, 2B and 3B) compared to the control group.
Figure 14:
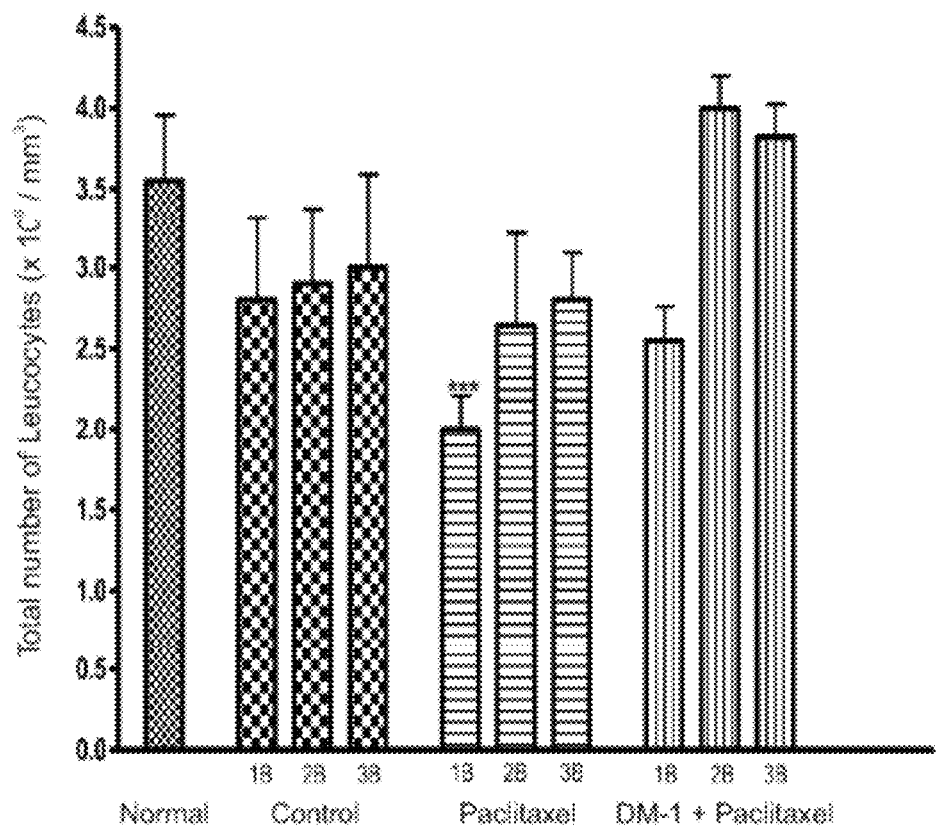
FIG. 14 shows the evaluation of the total white blood cells of normal mice and B16F10 melanoma tumor in groups of animals pre-treated with paclitaxel and placitaxel in association with DM1 on days 2, 6 and 10 after initiation of treatment (1B, 2B and 3B) compared to the control group.

The analysis of the number of leukocytes in animals treated with the compound DM-1 showed that the compound DM-1 leads to significant changes in leukocyte numbers compared to the control group. The change in the number of white blood cells of animals pre-treated groups of DM-1 and pre and post treated with DM-1 and paclitaxel in combination with DM-1 shows that the compound DM-1 has immunomodulatory properties (FIGS. 13 and 14).

Figure 15:
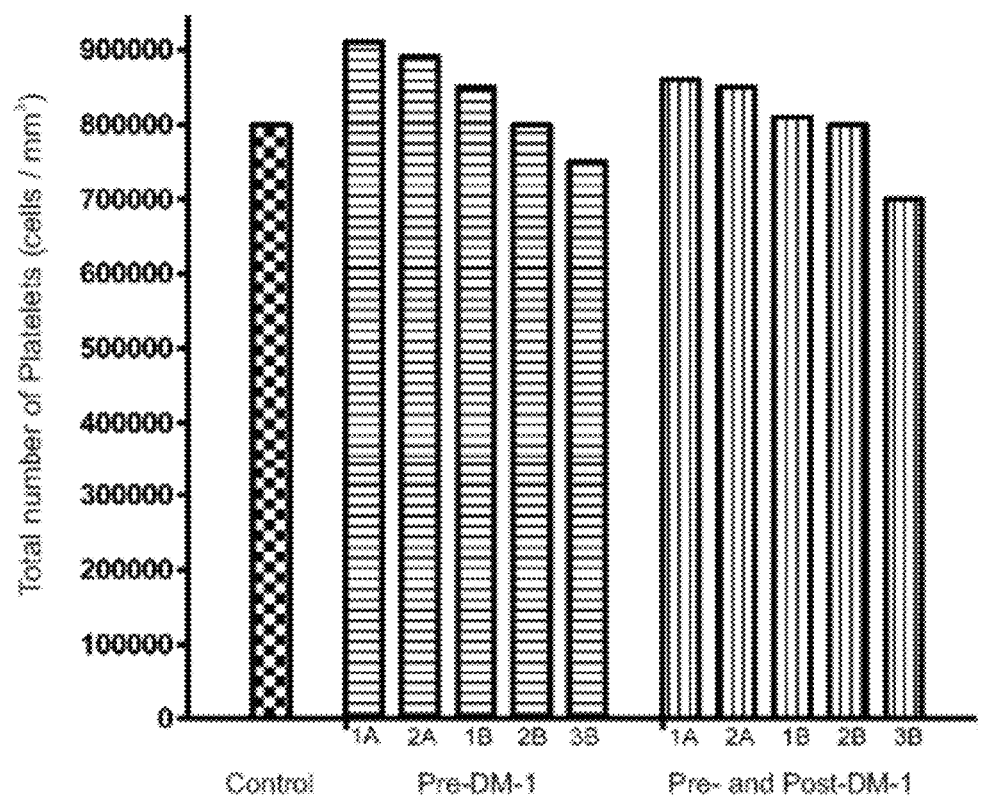
FIG. 15 shows the evaluation of the total number of platelets of normal mice and tumor melanoma B16F10 in groups of animals pre-treated with the compound DM-1 and pre and post treated with DM-1 on days 6 and 14 prior to implant (1a and 2A) and on days 2, 6 and 10 after initiation of treatment (1B, 2B and 3B) compared to the control group.
Figure 16:
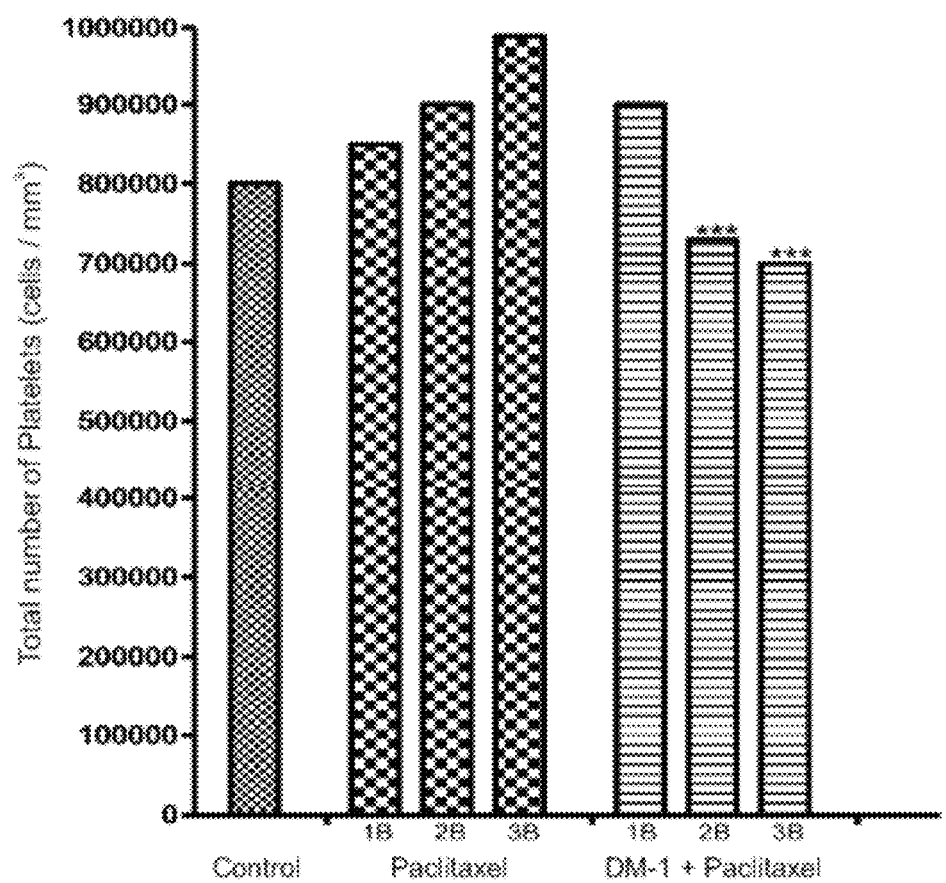
FIG. 16 shows the evaluation of the total number of platelets and normal animals with B16F10 melanoma tumor in groups of animals pre-treated with paclitaxel and placitaxel in association with DM1 on days 2, 6 and 10 after initiation of treatment (1B, 2B and 3B) compared to the control group.
Figure 17:
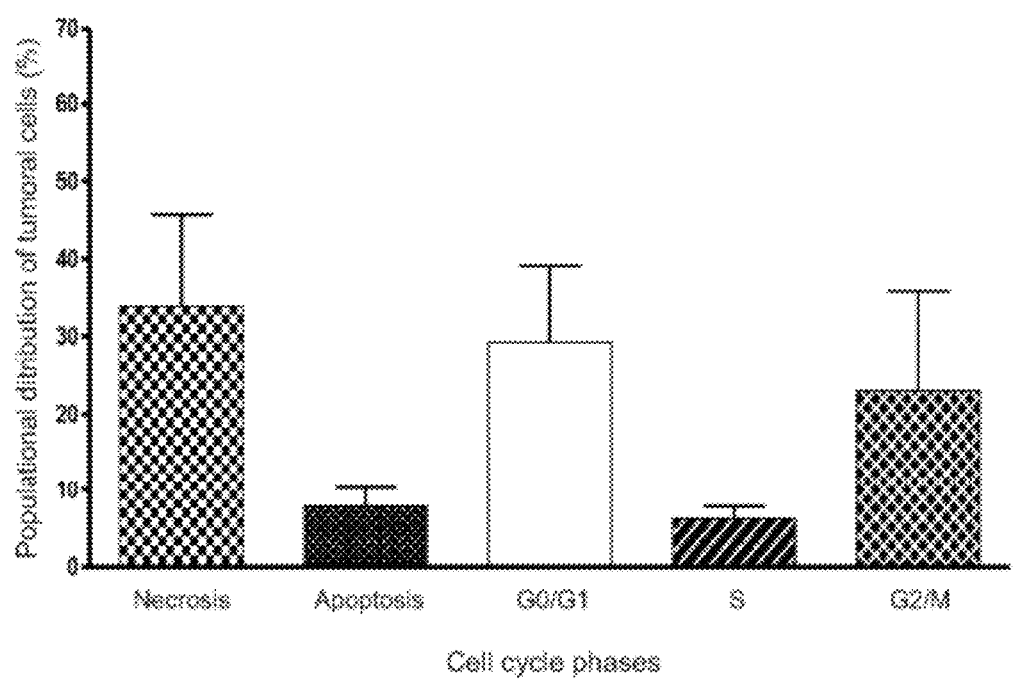
FIG. 17 shows the analysis of the distribution of B16F10 tumor cells of the dorsal tumors in the control group at different stages of the cell cycle.
Figure 18:
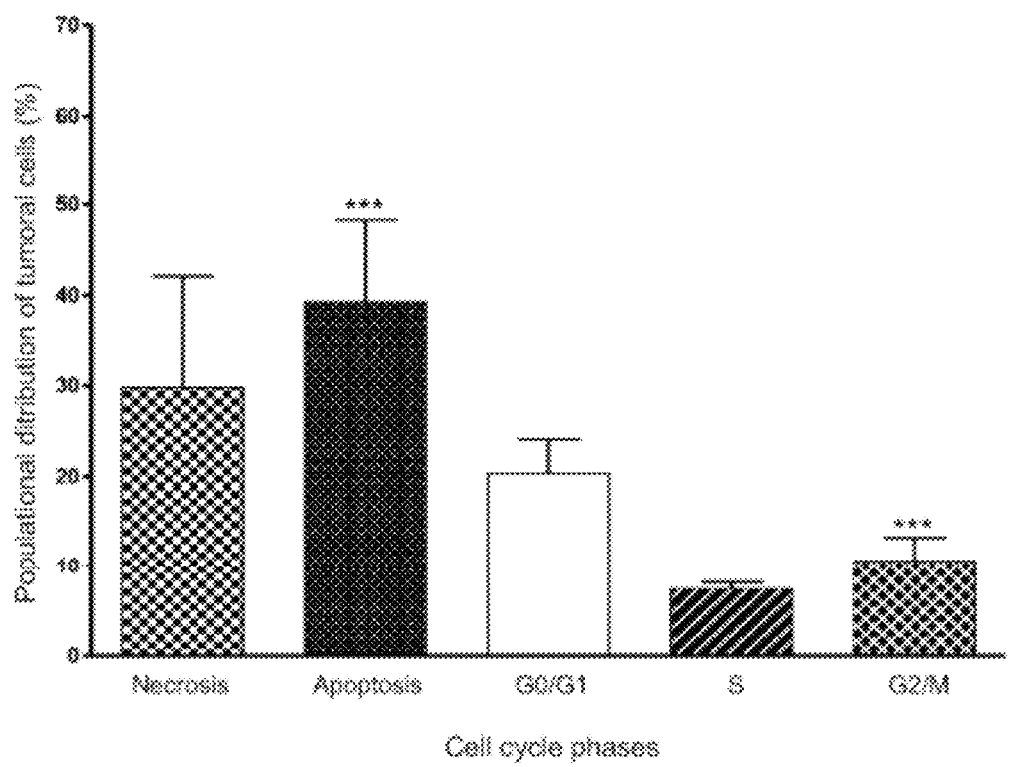
FIG. 18 shows the analysis of the distribution of B16F10 tumor cells of dorsal tumors of the pre-treated group with DM-1 at different stages of the cell cycle.
Figure 19:
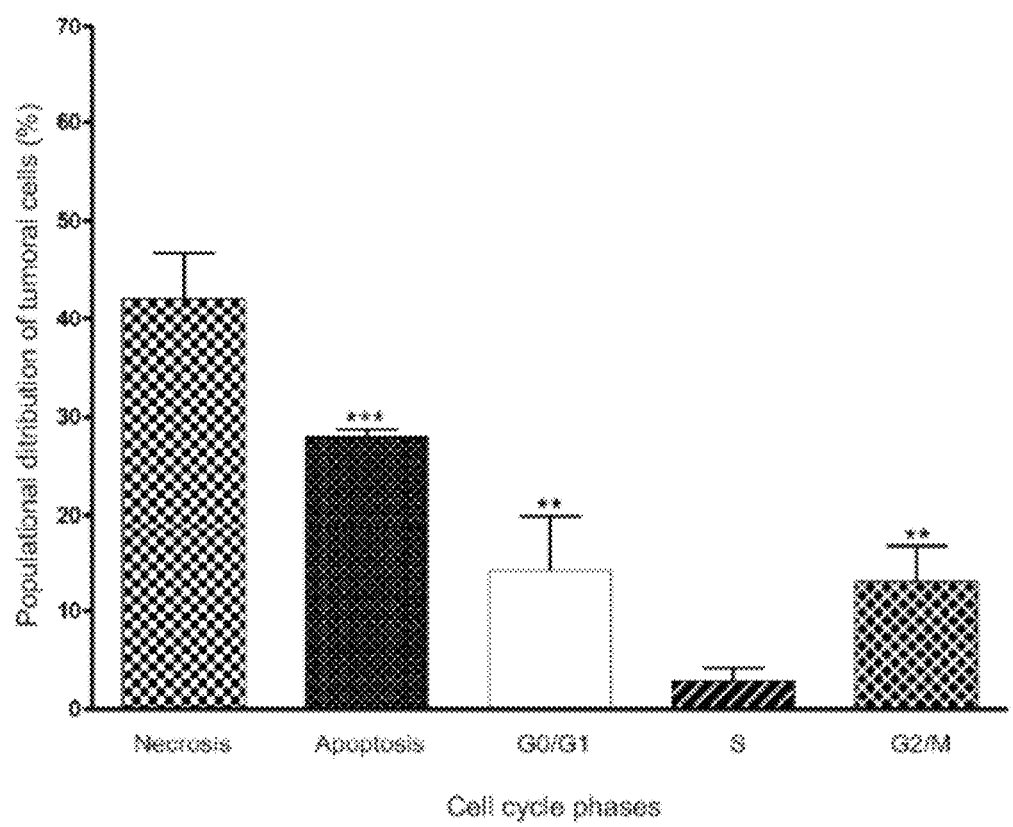
FIG. 19 shows the analysis of the distribution of B16F10 tumor cells of dorsal tumors of the groups pre- and post-treated with DM-1 at different stages of the cell cycle.
Figure 20:
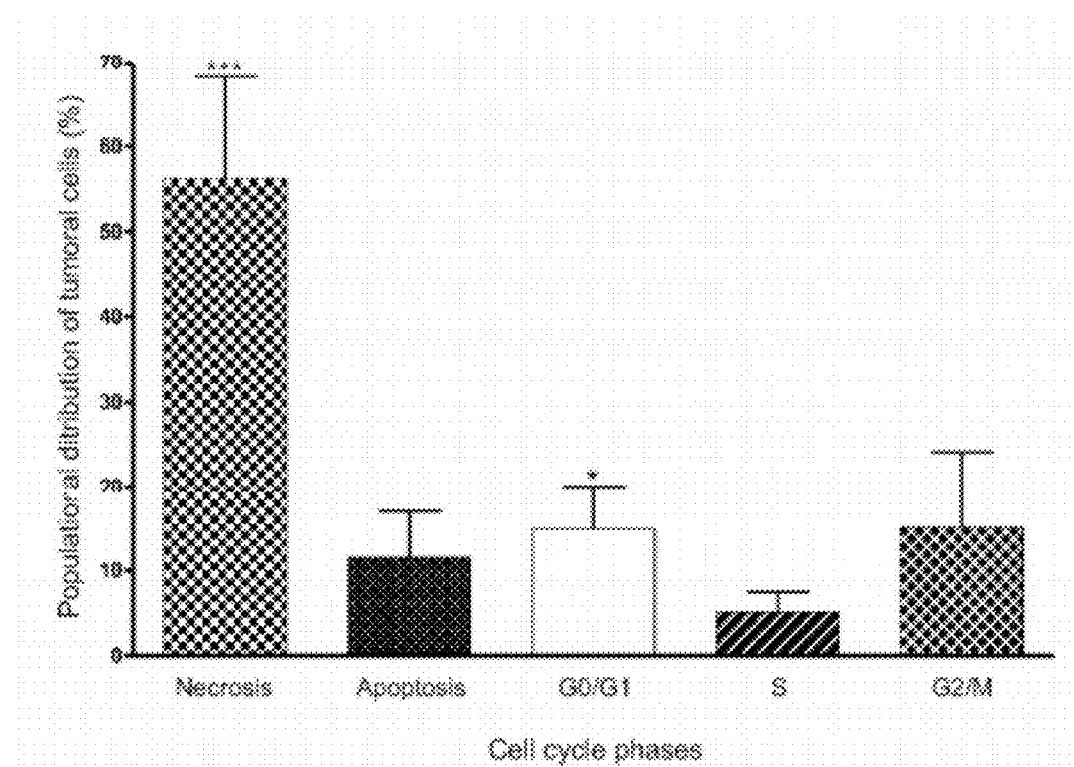
FIG. 20 shows the analysis of the distribution of B16F10 tumor cells of the group of dorsal tumors treated with paclitaxel in the different phases of the cell cycle.
Figure 21:
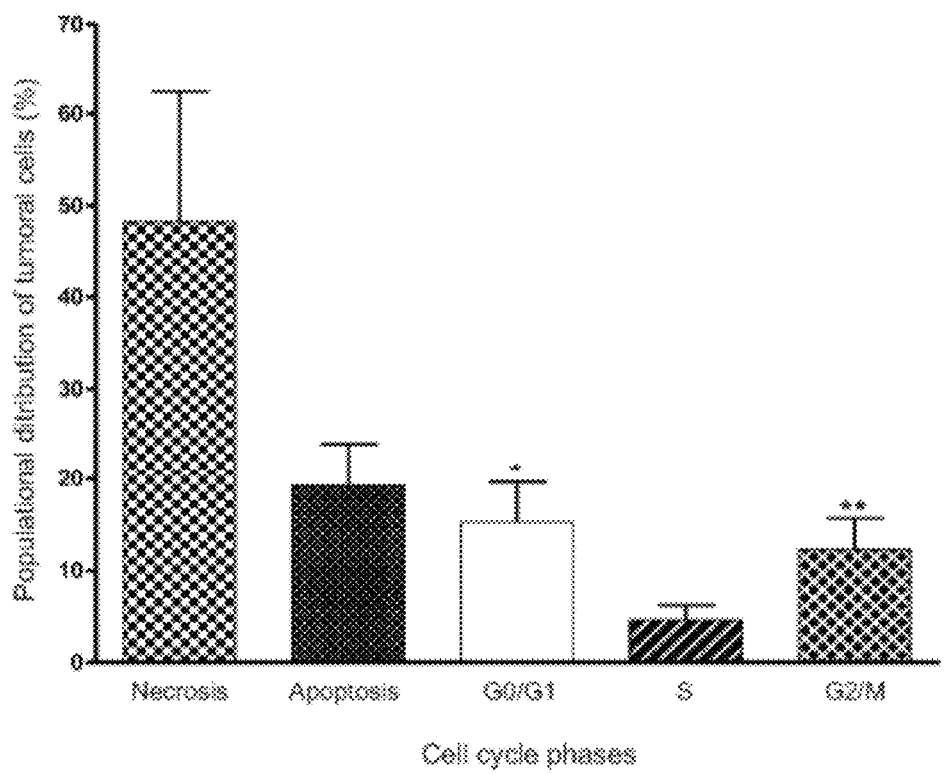
FIG. 21 shows the analysis of the distribution of B16F10 tumor cells of the group of dorsal tumors treated with paclitaxel in combination with DM-1 at different stages of the cell cycle.

The analysis of the number of platelets treated with the compound DM-1 showed that the compound DM-1 leads to significant reductions in platelet counts during treatment, compared to the control group. Treatment with paclitaxel alone, on the other hand, induced an increase in the number of platelets. These data corroborate the analysis performed by means of autopsies in the different experimental groups, reinforcing the inhibitory capacity of progression and metastasis formation after administration of the compound DM-1 (FIGS. 15 and 16).

h) Analysis of the Phases of the Cell Cycle and Apoptosis

Suspensions of 106 B16F10 melanoma cells were removed from all groups of animals subjected to various experimental protocols described above (group pre-treated with DM-1, group pre and post treated with DM-1, placitaxel treated group, the group treated with placitaxel in association with DM-1 and control group). The cells were then frozen and kept in liquid nitrogen. After incubation with propidium iodide, the analysis was performed on a FACSCalibur cytometer. The results were expressed as mean percentage of cells in different phases of the cell cycle, debris and necrosis, apoptosis (sub-G1), quiescent non-proliferating cells G0/G1, S phase—synthesis of genetic material and G2/M at the beginning of cell division.

The results showed that treatment with the paclitaxel chemotherapy induced significant increase in the proportion of cells killed by necrosis compared to control groups and treated with the DM-1 compound.

Apoptosis is the programmed death of a cell when there is damage to DNA, RNA or protein formation. It differs from necrosis by being characterized by decreased volume of the nucleus, fragmentation thereof, alteration of the permeability of the plasma membrane and cytoplasmic slow dissolution, without the abrupt phenomena that characterize the cell lysis. The tumor cells can prevent apoptosis and thus continue their proliferation in the tissue. Induce apoptosis in tumor cells is extremely difficult. The percentage of cells in G1 phase or sub-apoptotic increased significantly after administration of the compound DM-1 pre-treated groups in the DM-1, pre and post treated with DM-1 and treated with paclitaxel in combination with DM-1. The protocols of treatment with the compound DM-1 increased the proportion of apoptosis as well, and reduce the proportion of quiescent cells in G0/G1 phase (FIGS. 17, 18, 19, 20 and 21). These data indicate that the compound DM-1 in combination with chemotherapeutic agents paclitaxel and etoposide is an excellent agent inducing apoptosis in tumor cells, without producing the same effect on normal cells.

Example 3

Antimutagenic Activity of DM-1 a) Animals and Experimental Design

This study was approved by the Ethics Committee, Protocol 184-07 of the Bandeirante University of São Paulo (UNI-BAN). All Experiments received approval by the Brazilian Committee of Animal Experimentation (protocol No. 478/08 and 479/08).

We used animals of the Wistar strain, males and females, with approximately 90 days old and weighing between 250 and 300 grams, maintained with water and food "ad libitum" and in accordance with the rules and procedures regarding the use of laboratory animals. The animals were divided into four groups:

Negative control group—6 animals treated with a single dose of 0.7% saline solution.

The group treated with the DM-1 compound—6 animals treated with a single dose of the compound DM-1.

Group pre-treated with DM-1 and treated with cyclophosphamide—6 animals treated with a single dose of the compound DM-1, administered 8 hours before a single dose of cyclophosphamide chemotherapy.

Group treated with cyclophosphamide (positive control)—6 animals treated with a single dose of cyclophosphamide chemotherapy.

b) Administration of the Compounds DM-1 and Cyclophosphamide

In all tests was administered 1 mL of the compound of interest intraperitoneally. The compound DM-1 was administered daily at a concentration of 140 µM/Kg. Cyclophosphamide was administered at a concentration of 190 µM/Kg. The compounds were administered separately. At the end of the experiment (24 and 48 hours), animals were euthanized by deep general anesthesia induced by a lethal dose of sodium tiopentabarbital (CRMV, 2008).

c) Evaluation of the Micronucleus Test for Mutagenicity

This study allowed us to analyze the action of mutagenic compounds under study. Mutagenic compounds when administered in experimental animals cause changes in chromatin that can be identified by the formation of a mass within the nucleus called the micronucleus. The emergence of this mass is quantified and analyzed for their proportion to the capacity of a given drug or not to be mutagenic.

For micronucleus study we used the technique reported by Ribeiro et al. (Environmental Mutagenesis. Ulbra Publisher. Canoas: 1st edition, 2003.) For the staining of slides was used the technique described by Rabello-Gay et al. Apud SILVA, J. C. of; SILVA, S. of C. Evaluation of possible genotoxic effects of Gergilim (*Sesamum indicum* L., 2003).

In the test, the effect of the chemical agent is observed in anucleate polychromatic erythrocytes (ECPs), which have relatively short life span, so that it contains any micronucleus that was generated as a result of recent chromosomal damage. For the staining of slides was used Giemsa stain diluted in phosphate buffer at pH 6.8, in the ratio 1:10, for a period of 15 minutes. After staining, the slides were washed in distilled water to remove excess dye. To read the slides used an optical microscope and perform counting and analysis of 1000 polychromatic erythrocytes per slide, considering the frequency of micronucleated polychromatic erythrocytes.

Figure 22:
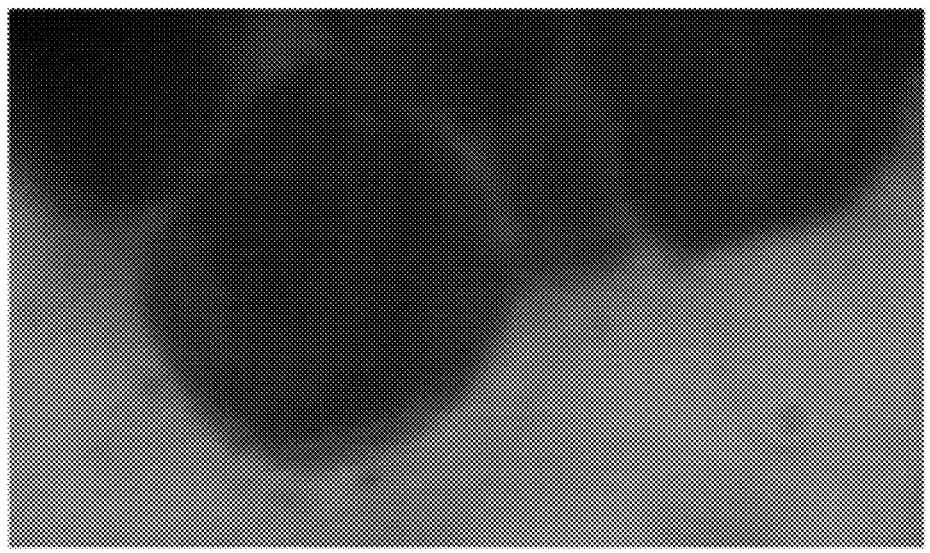
FIG. 22 shows the general aspects of erythroblast morphology of the negative control group. Giemsa staining at 400× magnification.
Figure 23:
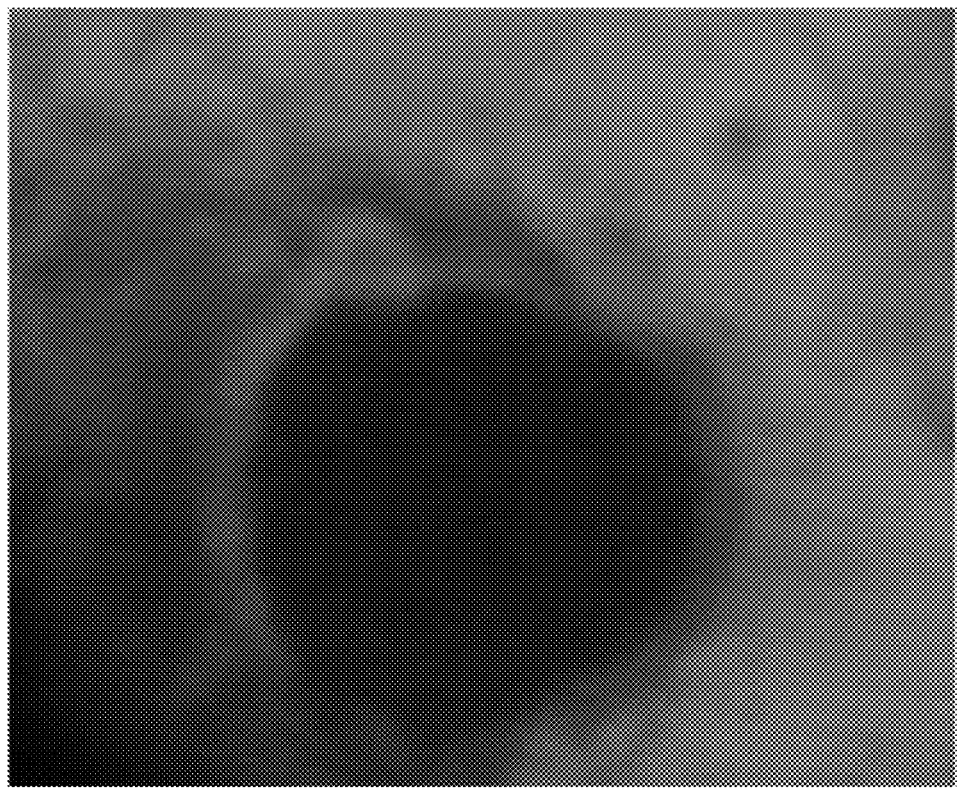
FIG. 23 shows the polychromatic erythroblast in bone marrow smear after administration of 140 μM/kg DM-1, intraperitoneally. Giemsa staining at 400× magnification.
Figure 24:
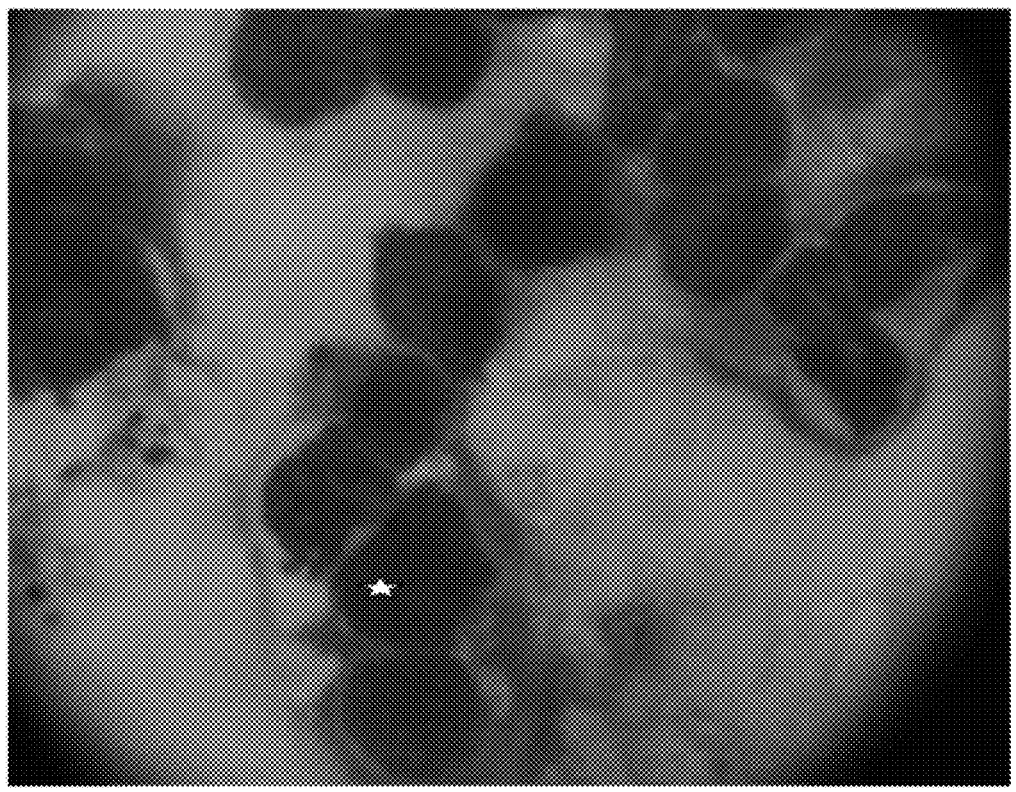
FIG. 24 shows erythroblasts and lymphoblasts (star) after administration of intact 140 μM/kg DM-1. Giemsa staining at 400× magnification.
Figure 25:
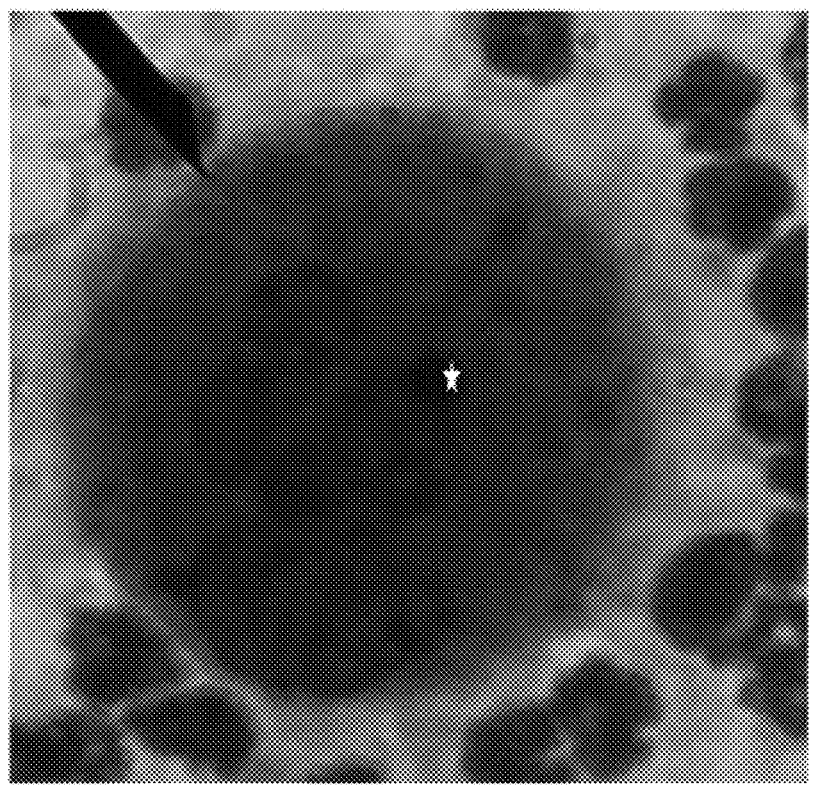
FIG. 25 shows the analysis of an erythroblast (arrow) after administration of cyclophosphamide 190 μM/kg. Giemsa staining at 400× magnification.
Figure 27:
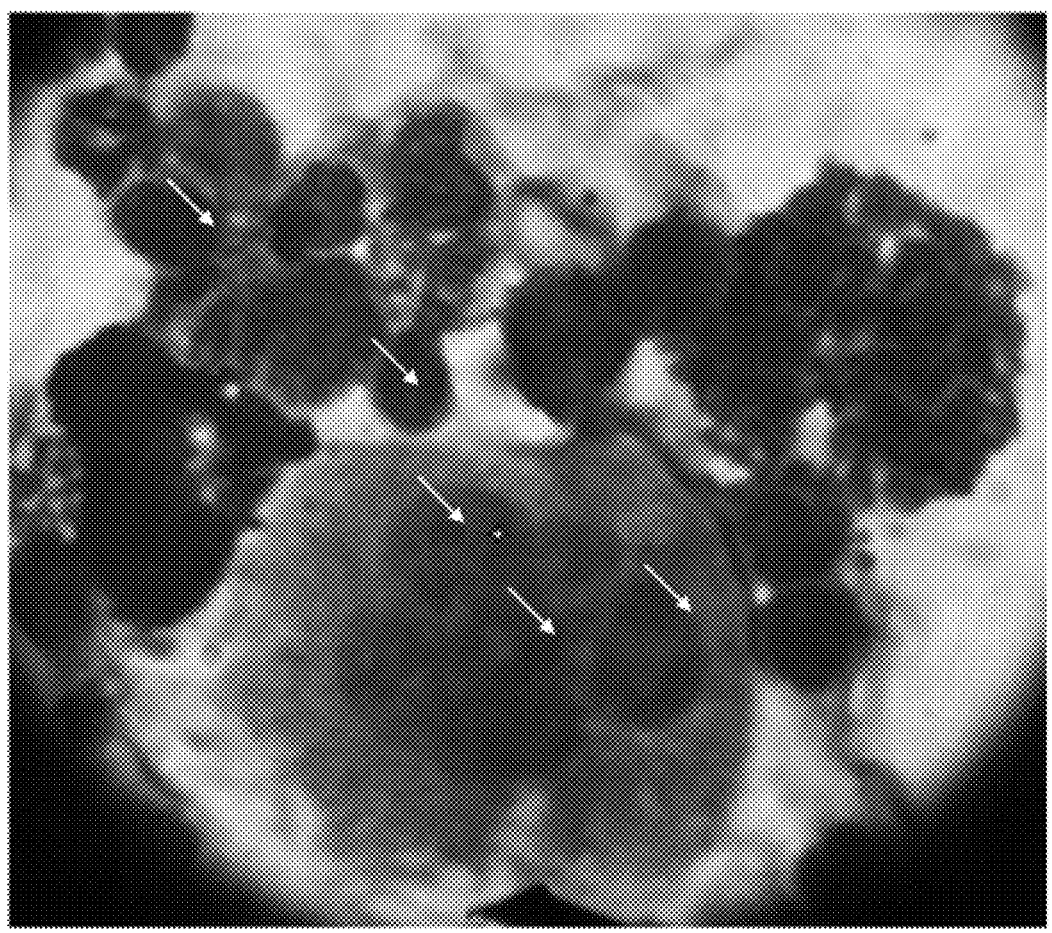
FIG. 27 shows erythrocytes by the action of cyclophosphamide administration 190 μM/kg, and high concentration of cells with micronuclei (arrows). Giemsa staining at 400× magnification.

The analysis was performed with cells increases 40× and 100× for the visualization of general morphology of the smears negative control group (FIG. 22), the groups treated with the compound DM1 and their polychromatic erythrocytes (FIGS. 23, 24 and 25). 1000 cells were analyzed per animal for the groups treated with DM1, negative control and cyclophosphamide for a total of 40,000 cells. The photodocumentation polychromatic erythrocytes was obtained by digital AVsoft. The group treated with cyclophosphamide was the positive control of the technique (FIG. 27). The results of the frequency of micronucleated polychromatic erythrocytes in 1000 cells was analyzed 36/1000. The negative control obtained a score of 2/1000 micronucleated polychromatic erythrocytes.

Table 1 shows the observed frequencies (For) of polychromatic erythrocytes with micronuclei in 1000 polychromatic erythrocytes for each animal treated with various compounds. The results were subjected to statistical analysis, the ANOVA test of variance followed by Tukey-Kramer multiple comparisons (parametric data) and the significance level of 5%, i.e., the probability P<0.05).

Table 1: Observed frequencies of polychromatic erythrocytes with micronuclei in 1000 polychromatic erythrocytes analysis in each rat treated with saline, DM-1 and/or cyclophosphamide.

| Frequency | 24 Hours | 48 Hours |
|---|---|---|
| Control | 2.3 ± 0.5 | 2.0 ± 0.5 |
| DM-1 | 2.4 ± 0.5 | 2.2 ± 0.5 |
| Cyclophosphamide + DM-1 | 3.5 ± 0.8 | 3.2 ± 1.0 |
| Cyclophosphamide | 36.5 ± 1.0*** | 35.5 ± 1.0*** |

***P < 0.0001 compared to DM-1 + Cyclophosphamide, DM-1 and negative control (ANOVA)

Figure 26:
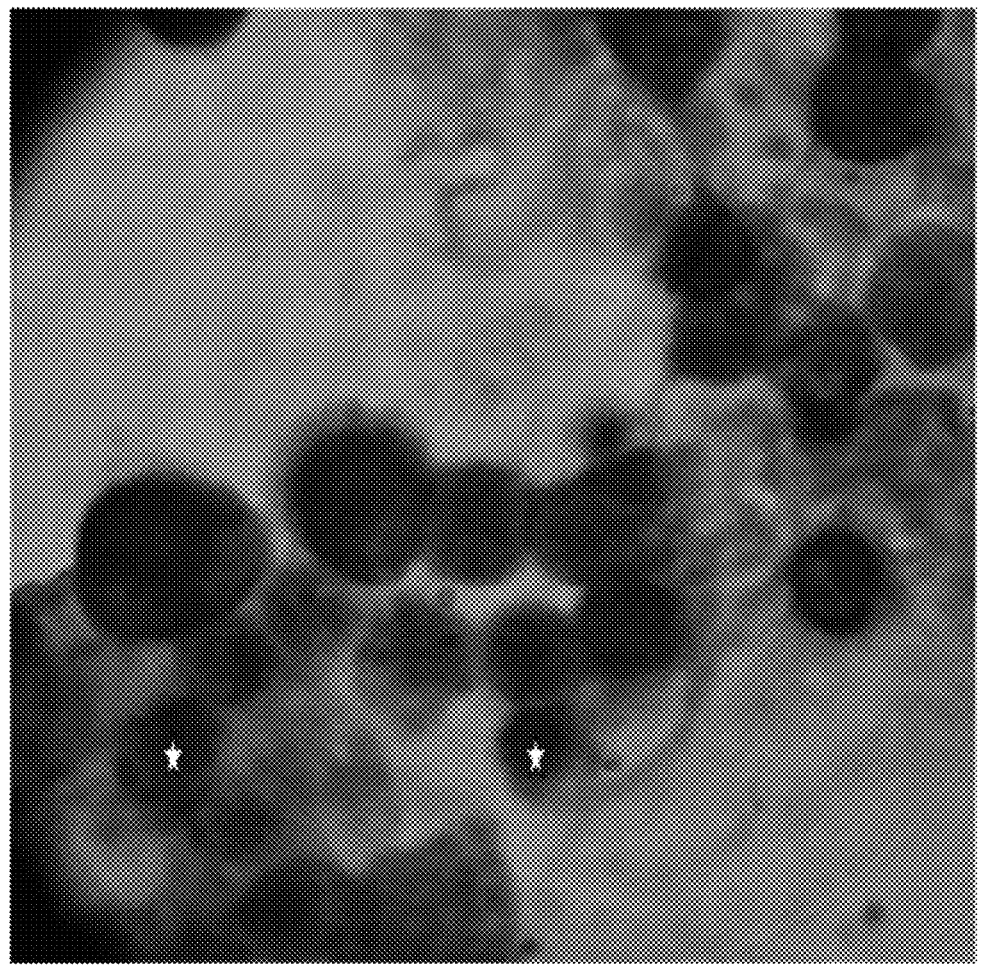
FIG. 26 shows a smear of bone marrow to the micronucleus test after administration of DM-1 140 μM/kg-eight hours after, administration of cyclophosphamide 190 μM/kg. Giemsa staining at 400× magnification.

We can observe a clear cellular changes after administration of cyclophosphamide, used as positive control. We observed a significant ordering in the formation of erythrocytes, the material extracted from bone marrow, when associated with the DM-1 compound. There is also a best response in the formation of young cells in the negative control. When the compound DM-1 was administered as a pre-treatment prior to administration of cyclophosphamide, there was a slight decrease of micronuclei (FIG. 26) and improved cell regeneration, resulting in a very positive response to the compound DM-1. We can conclude that the compound DM-1 presents a great preservation of bone marrow and a marked decrease in action of clastogenic effects. After the tests performed by the method of assessing the presence of micronuclei in bone marrow smears in animals treated with the compound DM-1, there were not found significant changes and the results are close to the negative control group, however in the group treated with cyclophosphamide, we did find the presence of more than 200 cells with micronuclei, confirming the mutagenic action. The group pre-treated with the compound DM-1 and 8 hours after treated with cyclophosphamide showed highly significant results, which leads us to conclude that the compound DM-1 has antimutagenic action, and provides excellent adjuvant action with other antitumor drugs trade has known, improving the ability of drug action, reducing side effects, resulting in an improved quality of life of the patient.

The invention claimed is:

1. A pharmaceutical composition comprising sodium 4-[5-(4-hydroxy-3-methoxy-phenyl)-3-oxo-penta-1,4-dienil]-2-methoxy-phenolate and paclitaxel, wherein paclitaxel and sodium 4-[5-(4-hydroxy-3-methoxy-phenyl)-3-oxo-penta-1,4-dienil]-2-methoxy-phenolate are in molar ratio from 15,000:1.6 to 15,000:0.83.

2. The pharmaceutical composition of claim 1, wherein the pharmaceutical composition is a cytoprotective agent.

3. The pharmaceutical composition of claim 1, wherein the pharmaceutical composition is an antimetastatic agent.

4. The pharmaceutical composition of claim 1, wherein the pharmaceutical composition is an antimutagenic agent.

5. The pharmaceutical composition of claim 1, wherein the pharmaceutical composition is an antitumor adjuvant composition.

6. A method of treatment of metastatic cancer, comprising administering to a subject in need thereof a polyfunctional metal phenolate and at least one anti-tumor drug, wherein the polyfunctional metal phenolate is sodium 4-[5-(4-hydroxy-3-methoxy-phenyl)-3-oxo-penta-1,4-dienil]-2-methoxy-phenolate and said at least one anti-tumor drug is paclitaxel, wherein paclitaxel and sodium 4-[5-(4-hydroxy-3-methoxy-phenyl)-3-oxo-penta-1,4-dienil]-2-methoxy-phenolate are in molar ratio from 15,000:1.6 to 15,000:0.83.

7. The method of claim 6, wherein the polyfunctional metal phenolate is a cytoprotective agent.

8. The method of claim 6, wherein the polyfunctional metal phenolate is an antimetastatic agent.

9. The method of claim 6, wherein the polyfunctional metal phenolate is an antimutagenic agent.

10. The method of claim 6, wherein the polyfunctional metal phenolate is an adjuvant antitumor agent.

* * * * *